US008473076B2

(12) United States Patent
Libbus et al.

(10) Patent No.: US 8,473,076 B2
(45) Date of Patent: *Jun. 25, 2013

(54) LEAD FOR STIMULATING THE BARORECEPTORS IN THE PULMONARY ARTERY

(75) Inventors: Imad Libbus, St. Paul, MN (US); Ronald W. Heil, Jr., Roseville, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/225,769

(22) Filed: Sep. 6, 2011

(65) Prior Publication Data

US 2011/0319960 A1 Dec. 29, 2011

Related U.S. Application Data

(63) Continuation of application No. 10/746,861, filed on Dec. 24, 2003, now Pat. No. 8,024,050.

(51) Int. Cl.
*A61N 1/05* (2006.01)
*A61N 1/04* (2006.01)

(52) U.S. Cl.
CPC ............... *A61N 1/0476* (2013.01); *A61N 1/056* (2013.01)
USPC ........................................... 607/148; 607/149

(58) Field of Classification Search
USPC ................................................. 607/148–149
See application file for complete search history.

(56) References Cited

U.S. PATENT DOCUMENTS

| | | | |
|---|---|---|---|
| 3,421,511 | A | 1/1969 | Schwartz et al. |
| 3,522,811 | A | 8/1970 | Seymour et al. |
| 3,557,796 | A | 1/1971 | Keller, Jr. et al. |
| 3,650,277 | A | 3/1972 | Sjostrand et al. |
| 4,357,946 | A | 11/1982 | Dutcher et al. |

(Continued)

FOREIGN PATENT DOCUMENTS

| | | | |
|---|---|---|---|
| EP | 0547734 | A2 | 6/1993 |
| EP | 1486232 | A2 | 12/2004 |

(Continued)

OTHER PUBLICATIONS

U.S. Appl. No. 10/700,368, Final Office Action mailed Oct. 15, 2008, 12 pgs.

(Continued)

*Primary Examiner* — Carl H Layno
*Assistant Examiner* — Jessica Sarcione
(74) *Attorney, Agent, or Firm* — Schwegman Lundberg & Woessner, P.A.

(57) ABSTRACT

An apparatus includes a flexible lead body extending from a proximal end to a distal end, an expandable electrode coupled proximate the distal end, the expandable electrode having an expanded diameter dimensioned to abut a wall of a pulmonary artery, and an implantable pulse generator electrically coupled to the expandable electrode. The expandable electrode includes a plurality of electrode zones. The plurality of zones can be tested to determine which zone delivers the best baroreflex response. At least one of the electrode zones can be selected to deliver a stimulation signal based on the testing. The implantable pulse generator is adapted to deliver a baroreflex stimulation signal to a baroreceptor in the pulmonary artery via the electrode.

18 Claims, 3 Drawing Sheets

630
640
632
634
636
A
B
C

U.S. PATENT DOCUMENTS 4,397,946 A 8/1983 Imada et al.
4,730,619 A 3/1988 Koning et al.
4,770,177 A 9/1988 Schroeppel
4,791,931 A 12/1988 Slate
4,936,304 A 6/1990 Kresh et al.
4,960,129 A 10/1990 dePaola et al.
4,972,834 A 11/1990 Begemann et al.
5,024,222 A 6/1991 Thacker
5,052,388 A 10/1991 Sivula et al.
5,111,815 A 5/1992 Mower
5,190,035 A 3/1993 Salo et al.
5,199,428 A 4/1993 Obel et al.
5,203,326 A 4/1993 Collins
5,243,980 A 9/1993 Mehra
5,318,592 A 6/1994 Schaldach
5,324,316 A 6/1994 Schulman et al.
5,330,507 A 7/1994 Schwartz
5,334,221 A 8/1994 Bardy
5,356,425 A 10/1994 Bardy et al.
5,374,282 A 12/1994 Nichols et al.
5,403,351 A 4/1995 Saksena
5,409,009 A 4/1995 Olson
5,411,531 A 5/1995 Hill et al.
5,437,285 A 8/1995 Verrier et al.
5,507,784 A 4/1996 Hill et al.
5,513,644 A 5/1996 McClure et al.
5,522,854 A 6/1996 Ideker et al.
5,540,730 A 7/1996 Terry, Jr. et al.
5,562,711 A 10/1996 Yerich et al.
5,578,061 A 11/1996 Stroetmann et al.
5,593,430 A 1/1997 Renger
5,651,378 A 7/1997 Matheny et al.
5,658,318 A 8/1997 Stroetmann et al.
5,662,689 A 9/1997 Elsberry et al.
5,690,681 A 11/1997 Geddes et al.
5,700,282 A 12/1997 Zabara
5,707,400 A 1/1998 Terry, Jr. et al.
5,749,900 A 5/1998 Schroeppel et al.
5,792,187 A 8/1998 Adams
5,817,131 A 10/1998 Elsberry et al.
5,902,324 A 5/1999 Thompson et al.
5,913,876 A 6/1999 Taylor et al.
5,916,239 A 6/1999 Geddes et al.
6,006,122 A 12/1999 Smits
6,006,134 A 12/1999 Hill et al.
6,035,233 A 3/2000 Schroeppel et al.
6,058,331 A 5/2000 King
6,073,048 A 6/2000 Kieval et al.
6,076,014 A 6/2000 Alt
6,104,956 A 8/2000 Naritoku et al.
6,134,470 A 10/2000 Hartlaub
6,141,590 A 10/2000 Renirie et al.
6,144,878 A 11/2000 Schroeppel et al.
6,161,042 A 12/2000 Hartley et al.
6,161,048 A 12/2000 Sluijter et al.
6,164,284 A 12/2000 Schulman et al.
6,169,918 B1 1/2001 Haefner et al.
6,178,349 B1 1/2001 Kieval
6,181,966 B1 1/2001 Nigam
6,240,314 B1 5/2001 Plicchi et al.
6,240,316 B1 5/2001 Richmond et al.
6,266,564 B1 7/2001 Hill et al.
6,272,377 B1 8/2001 Sweeney et al.
6,285,907 B1 9/2001 Kramer et al.
6,285,909 B1 9/2001 Sweeney et al.
6,292,695 B1 9/2001 Webster, Jr. et al.
6,292,703 B1 9/2001 Meier et al.
6,308,104 B1 10/2001 Taylor et al.
6,341,236 B1 1/2002 Osorio et al.
6,349,233 B1 2/2002 Adams
6,371,922 B1 4/2002 Baumann et al.
6,381,499 B1 4/2002 Taylor et al.
6,400,982 B2 6/2002 Sweeney et al.
6,405,079 B1 6/2002 Ansarinia
6,411,845 B1 6/2002 Mower
6,421,557 B1 7/2002 Meyer
6,438,423 B1 8/2002 Rezai et al.
6,442,424 B1 8/2002 Ben-Haim et al.
6,447,443 B1 9/2002 Keogh et al.
6,449,507 B1 9/2002 Hill et al.
6,473,644 B1 10/2002 Terry, Jr. et al.
6,477,418 B2 11/2002 Plicchi et al.
6,487,442 B1 11/2002 Wood
6,487,446 B1 11/2002 Hill et al.
6,487,450 B1 11/2002 Chen et al.
6,493,585 B2 12/2002 Plicchi et al.
6,511,500 B1 1/2003 Rahme
6,522,926 B1 2/2003 Kieval et al.
6,532,388 B1 3/2003 Hill et al.
6,542,774 B2 4/2003 Hill et al.
6,564,096 B2 5/2003 Mest
6,571,121 B2 5/2003 Schroeppel et al.
6,571,122 B2 5/2003 Schroeppel et al.
6,574,512 B1 6/2003 Zhang et al.
6,584,362 B1 6/2003 Scheiner et al.
6,600,954 B2 7/2003 Cohen et al.
6,610,713 B2 8/2003 Tracey
6,611,713 B2 8/2003 Schauerte
6,622,041 B2 9/2003 Terry, Jr. et al.
6,628,987 B1 9/2003 Hill et al.
6,662,052 B1 12/2003 Sarwal et al.
6,668,191 B1 12/2003 Boveja
6,684,105 B2 1/2004 Cohen et al.
6,690,971 B2 2/2004 Schauerte et al.
6,718,203 B2 4/2004 Weiner et al.
6,718,207 B2 4/2004 Connelly
6,718,208 B2 4/2004 Hill et al.
6,735,471 B2 5/2004 Hill et al.
6,763,268 B2 7/2004 MacDonald et al.
6,778,854 B2 8/2004 Puskas
6,788,970 B1 9/2004 Park et al.
6,799,069 B2 9/2004 Weiner et al.
6,804,561 B2 10/2004 Stover
RE38,654 E 11/2004 Hill et al.
6,838,471 B2 1/2005 Tracey
6,839,592 B2 1/2005 Grandjean
6,845,267 B2 1/2005 Harrison et al.
RE38,705 E 2/2005 Hill et al.
6,882,886 B1 4/2005 Witte et al.
6,885,888 B2 4/2005 Rezai
6,904,318 B2 6/2005 Hill et al.
6,912,419 B2 6/2005 Hill et al.
6,922,585 B2 7/2005 Zhou et al.
6,928,320 B2 8/2005 King
6,928,326 B1 8/2005 Levine
6,934,583 B2 8/2005 Weinberg et al.
6,937,896 B1 8/2005 Kroll
6,942,622 B1 9/2005 Turcott
6,985,774 B2 1/2006 Kieval et al.
7,025,730 B2 4/2006 Cho et al.
7,058,450 B2 6/2006 Struble et al.
7,072,720 B2 7/2006 Puskas
7,092,755 B2 8/2006 Florio
7,136,704 B2 11/2006 Schulman
7,139,607 B1 11/2006 Shelchuk
7,155,284 B1 12/2006 Whitehurst et al.
7,158,832 B2 1/2007 Kieval et al.
7,167,756 B1 1/2007 Torgerson et al.
7,194,313 B2 3/2007 Libbus
7,245,967 B1 7/2007 Shelchuk
7,260,431 B2 8/2007 Libbus et al.
7,277,761 B2 10/2007 Shelchuk
7,294,334 B1 11/2007 Michal et al.
7,299,086 B2 11/2007 McCabe et al.
7,321,793 B2 1/2008 Ben Ezra et al.
7,333,854 B1 2/2008 Brewer et al.
7,340,299 B2 3/2008 Puskas
7,403,819 B1 7/2008 Shelchuk et al.
7,460,906 B2 12/2008 Libbus
7,480,532 B2 1/2009 Kieval et al.
7,486,991 B2 2/2009 Libbus et al.
7,493,161 B2 2/2009 Libbus et al.
7,499,748 B2 3/2009 Moffitt et al.
7,509,166 B2 3/2009 Libbus
7,542,800 B2 6/2009 Libbus et al.
7,548,780 B2 6/2009 Libbus et al.
7,551,958 B2 6/2009 Libbus et al.

7,555,341 B2 6/2009 Moffitt et al.
7,561,923 B2 7/2009 Libbus et al.
7,570,999 B2 8/2009 Libbus et al.
7,572,228 B2 8/2009 Wolinsky et al.
7,584,004 B2 9/2009 Caparso et al.
7,587,238 B2 9/2009 Moffitt et al.
7,643,875 B2 1/2010 Heil, Jr. et al.
7,647,114 B2 1/2010 Libbus
7,657,312 B2 2/2010 Pastore et al.
7,706,884 B2 4/2010 Libbus
7,734,348 B2 6/2010 Zhang et al.
7,765,000 B2 7/2010 Zhang et al.
7,769,450 B2 8/2010 Libbus et al.
7,783,353 B2 8/2010 Libbus et al.
7,869,881 B2 1/2011 Libbus et al.
8,024,050 B2 9/2011 Libbus et al.
8,121,693 B2 2/2012 Libbus
8,126,559 B2 2/2012 Libbus
8,126,560 B2 2/2012 Scheiner et al.
8,131,362 B2 3/2012 Moffitt et al.
8,131,373 B2 3/2012 Libbus
8,195,289 B2 6/2012 Heil, Jr. et al.
8,285,389 B2 10/2012 Libbus et al.
8,321,023 B2 11/2012 Libbus et al.
2001/0020136 A1 9/2001 Sweeney et al.
2002/0004670 A1 1/2002 Florio et al.
2002/0010493 A1 1/2002 Poezevara et al.
2002/0016344 A1 2/2002 Tracey
2002/0016550 A1 2/2002 Sweeney et al.
2002/0026221 A1 2/2002 Hill et al.
2002/0026222 A1 2/2002 Schauerte et al.
2002/0026228 A1 2/2002 Schauerte
2002/0032468 A1 3/2002 Hill et al.
2002/0042637 A1 4/2002 Stover
2002/0058877 A1 5/2002 Baumann et al.
2002/0068875 A1 6/2002 Schroeppel et al.
2002/0072776 A1 6/2002 Osorio et al.
2002/0077670 A1 6/2002 Archer et al.
2002/0082661 A1 6/2002 Plicchi et al.
2002/0091415 A1 7/2002 Lovett et al.
2002/0095139 A1 7/2002 Keogh et al.
2002/0107553 A1 8/2002 Hill et al.
2002/0107557 A1 8/2002 Edell et al.
2002/0111661 A1* 8/2002 Cross et al. .................. 607/117
2002/0116030 A1 8/2002 Rezai
2002/0120304 A1 8/2002 Mest
2002/0123769 A1 9/2002 Panken et al.
2002/0138109 A1 9/2002 Keogh et al.
2002/0143369 A1 10/2002 Hill et al.
2002/0161410 A1 10/2002 Kramer et al.
2002/0165586 A1 11/2002 Hill et al.
2002/0183237 A1 12/2002 Puskas
2002/0183793 A1 12/2002 Struble et al.
2002/0188325 A1 12/2002 Hill et al.
2002/0188326 A1 12/2002 Zheng et al.
2002/0193843 A1 12/2002 Hill et al.
2002/0198570 A1 12/2002 Puskas
2002/0198571 A1 12/2002 Puskas
2003/0003052 A1 1/2003 Hampton
2003/0004549 A1 1/2003 Hill et al.
2003/0018368 A1 1/2003 Ansarinia
2003/0023279 A1 1/2003 Spinelli et al.
2003/0036773 A1 2/2003 Whitehurst et al.
2003/0040774 A1 2/2003 Terry et al.
2003/0045909 A1 3/2003 Gross et al.
2003/0045914 A1 3/2003 Cohen et al.
2003/0060848 A1 3/2003 Kieval et al.
2003/0060857 A1 3/2003 Perrson et al.
2003/0060858 A1 3/2003 Kieval et al.
2003/0074039 A1 4/2003 Puskas
2003/0078623 A1 4/2003 Weinberg et al.
2003/0078629 A1 4/2003 Chen
2003/0100924 A1 5/2003 Foreman et al.
2003/0105493 A1 6/2003 Salo
2003/0114905 A1 6/2003 Kuzma
2003/0125770 A1 7/2003 Fuimaono et al.
2003/0149450 A1 8/2003 Mayberg
2003/0158584 A1 8/2003 Cates et al.
2003/0176818 A1 9/2003 Schuler et al.
2003/0181951 A1 9/2003 Cates
2003/0191403 A1 10/2003 Zhou et al.
2003/0191404 A1 10/2003 Klein
2003/0195571 A1 10/2003 Burnes et al.
2003/0195578 A1 10/2003 Perron et al.
2003/0212440 A1 11/2003 Boveja
2003/0212445 A1 11/2003 Weinberg
2003/0216790 A1 11/2003 Hill et al.
2003/0216792 A1 11/2003 Levin et al.
2003/0229380 A1 12/2003 Adams et al.
2003/0236558 A1 12/2003 Whitehurst et al.
2004/0010303 A1 1/2004 Bolea et al.
2004/0015204 A1 1/2004 Whitehurst et al.
2004/0015205 A1 1/2004 Whitehurst et al.
2004/0019364 A1 1/2004 Kieval et al.
2004/0024422 A1 2/2004 Hill et al.
2004/0030362 A1 2/2004 Hill et al.
2004/0038857 A1 2/2004 Tracey
2004/0048795 A1 3/2004 Ivanova et al.
2004/0049120 A1 3/2004 Cao et al.
2004/0049235 A1 3/2004 Deno et al.
2004/0054381 A1 3/2004 Pastore et al.
2004/0059383 A1 3/2004 Puskas
2004/0068299 A1 4/2004 Laske et al.
2004/0088009 A1 5/2004 Degroot
2004/0088015 A1 5/2004 Casavant et al.
2004/0111118 A1 6/2004 Hill et al.
2004/0116970 A1 6/2004 Girouard et al.
2004/0122496 A1 6/2004 Zhang et al.
2004/0122497 A1 6/2004 Zhang et al.
2004/0122498 A1 6/2004 Zhang et al.
2004/0127942 A1 7/2004 Yomtov et al.
2004/0127947 A1 7/2004 Kim et al.
2004/0133248 A1 7/2004 Frei et al.
2004/0138719 A1 7/2004 Cho et al.
2004/0138721 A1 7/2004 Osorio et al.
2004/0162584 A1 8/2004 Hill et al.
2004/0162594 A1 8/2004 King
2004/0172074 A1 9/2004 Yoshihito
2004/0172075 A1 9/2004 Shafer et al.
2004/0172094 A1 9/2004 Cohen et al.
2004/0186517 A1 9/2004 Hill et al.
2004/0186531 A1 9/2004 Jahns et al.
2004/0193231 A1 9/2004 David et al.
2004/0199209 A1 10/2004 Hill et al.
2004/0199210 A1 10/2004 Shelchuk
2004/0215288 A1* 10/2004 Lee et al. ........................ 607/48
2004/0215289 A1 10/2004 Fukui
2004/0220621 A1 11/2004 Zhou et al.
2004/0243182 A1 12/2004 Cohen et al.
2004/0243206 A1 12/2004 Tadlock
2004/0249416 A1 12/2004 Yun et al.
2004/0249429 A1 12/2004 Tadlock
2004/0254612 A1 12/2004 Ezra et al.
2004/0254616 A1 12/2004 Rossing et al.
2004/0260374 A1 12/2004 Zhang et al.
2004/0260375 A1 12/2004 Zhang et al.
2005/0010263 A1 1/2005 Schauerte
2005/0015129 A1 1/2005 Mische
2005/0021092 A1 1/2005 Yun et al.
2005/0055060 A1 3/2005 Koh et al.
2005/0059897 A1 3/2005 Snell et al.
2005/0065553 A1 3/2005 Ben Ezra et al.
2005/0065555 A1 3/2005 Er
2005/0065562 A1 3/2005 Rezai
2005/0065573 A1 3/2005 Rezai
2005/0065575 A1 3/2005 Dobak
2005/0075701 A1 4/2005 Shafer
2005/0075702 A1 4/2005 Shafer
2005/0085864 A1 4/2005 Schulman et al.
2005/0096705 A1 5/2005 Pastore et al.
2005/0096707 A1 5/2005 Hill et al.
2005/0125044 A1 6/2005 Tracey
2005/0131467 A1 6/2005 Boveja
2005/0143412 A1 6/2005 Puskas
2005/0143779 A1 6/2005 Libbus
2005/0143785 A1 6/2005 Libbus
2005/0143787 A1 6/2005 Boveja et al.
2005/0149126 A1 7/2005 Libbus 2005/0149127 A1 7/2005 Libbus
2005/0149128 A1 7/2005 Heil, Jr. et al.
2005/0149129 A1 7/2005 Libbus et al.
2005/0149130 A1 7/2005 Libbus
2005/0149131 A1 7/2005 Libbus et al.
2005/0149132 A1 7/2005 Libbus
2005/0149133 A1 7/2005 Libbus et al.
2005/0149143 A1 7/2005 Libbus et al.
2005/0149148 A1 7/2005 King
2005/0149155 A1 7/2005 Scheiner et al.
2005/0149156 A1 7/2005 Libbus et al.
2005/0154418 A1 7/2005 Kieval et al.
2005/0182288 A1 8/2005 Zabara
2005/0187584 A1 8/2005 Denker et al.
2005/0187586 A1 8/2005 David et al.
2005/0197600 A1 9/2005 Schuler et al.
2005/0197675 A1 9/2005 David et al.
2005/0222632 A1 10/2005 Obino
2005/0251216 A1 11/2005 Hill et al.
2005/0261741 A1 11/2005 Libbus et al.
2006/0074453 A1 4/2006 Kieval et al.
2006/0079945 A1 4/2006 Libbus
2006/0089678 A1 4/2006 Shalev
2006/0106428 A1 5/2006 Libbus et al.
2006/0106429 A1 5/2006 Libbus et al.
2006/0116737 A1 6/2006 Libbus
2006/0122675 A1 6/2006 Libbus et al.
2006/0134071 A1 6/2006 Ross et al.
2006/0134079 A1 6/2006 Sih et al.
2006/0136027 A1 6/2006 Westlund et al.
2006/0136028 A1 6/2006 Ross et al.
2006/0217772 A1 9/2006 Libbus et al.
2006/0253156 A1 11/2006 Pastore et al.
2006/0259107 A1 11/2006 Caparso et al.
2006/0271108 A1 11/2006 Libbus et al.
2006/0271115 A1 11/2006 Ben-Ezra et al.
2006/0271118 A1 11/2006 Libbus et al.
2006/0282131 A1 12/2006 Caparso et al.
2007/0021790 A1 1/2007 Kieval et al.
2007/0021792 A1 1/2007 Kieval et al.
2007/0021796 A1 1/2007 Kieval et al.
2007/0021797 A1 1/2007 Kieval et al.
2007/0021798 A1 1/2007 Kieval et al.
2007/0021799 A1 1/2007 Kieval et al.
2007/0034261 A1 2/2007 Eichler
2007/0038259 A1 2/2007 Kieval et al.
2007/0038260 A1 2/2007 Kieval et al.
2007/0038261 A1 2/2007 Kieval et al.
2007/0038262 A1 2/2007 Kieval et al.
2007/0060972 A1 3/2007 Kieval et al.
2007/0067008 A1 3/2007 Scheiner et al.
2007/0068260 A1 3/2007 Hong et al.
2007/0093875 A1 4/2007 Chavan et al.
2007/0142864 A1 6/2007 Libbus et al.
2007/0142871 A1 6/2007 Libbus et al.
2007/0167984 A1 7/2007 Kieval et al.
2007/0191904 A1 8/2007 Libbus et al.
2008/0021507 A1 1/2008 Libbus et al.
2008/0086174 A1 4/2008 Libbus et al.
2008/0125843 A1 5/2008 Ben-David et al.
2008/0147140 A1 6/2008 Ternes et al.
2008/0167694 A1 7/2008 Bolea et al.
2008/0177350 A1 7/2008 Kieval et al.
2008/0200960 A1 8/2008 Libbus
2008/0228238 A1 9/2008 Libbus
2008/0243196 A1 10/2008 Libbus et al.
2009/0048641 A1 2/2009 Libbus
2009/0132002 A1 5/2009 Kieval
2009/0143834 A1 6/2009 Libbus
2009/0143838 A1 6/2009 Libbus et al.
2009/0198294 A1 8/2009 Rossing et al.
2009/0306734 A1 12/2009 Moffitt
2010/0076511 A1 3/2010 Heil, Jr. et al.
2010/0106226 A1 4/2010 Libbus
2010/0125307 A1 5/2010 Pastore et al.
2010/0185255 A1 7/2010 Libbus
2010/0222832 A1 9/2010 Zhang et al.
2010/0274321 A1 10/2010 Libbus
2010/0286740 A1 11/2010 Libbus et al.
2010/0298898 A1 11/2010 Libbus
2011/0082514 A1 4/2011 Libbus et al.
2011/0295333 A1 12/2011 Libbus
2012/0123495 A1 5/2012 Libbus
2012/0165888 A1 6/2012 Libbus
2012/0239099 A1 9/2012 Heil, Jr. et al.

FOREIGN PATENT DOCUMENTS

EP 1541193 A1 6/2005
EP 1706177 A1 10/2006
GB 1297991 11/1972
JP 49015438 4/1974
JP 05269210 10/1993
JP 8-52121 2/1996
JP 2005519680 7/2005
JP 2005521489 7/2005
JP 201220185 A 2/2012
WO WO-9216257 A1 10/1992
WO WO-9713550 A1 4/1997
WO WO-9740885 A1 11/1997
WO WO-0124876 A1 4/2001
WO WO-0176689 A2 10/2001
WO WO-0226314 A1 4/2002
WO WO-0226318 A1 4/2002
WO WO-0226320 A1 4/2002
WO WO-0234327 A2 5/2002
WO WO-02085448 A2 10/2002
WO WO-03011388 A2 2/2003
WO WO-03026741 A1 4/2003
WO WO-03041559 A2 5/2003
WO WO-03076008 A1 9/2003
WO WO-03082080 A2 10/2003
WO WO-03082080 A3 10/2003
WO WO-03082403 A2 10/2003
WO WO-03099373 A2 12/2003
WO WO-03099377 A1 12/2003
WO WO-2004012814 A1 2/2004
WO WO-2004084990 A1 10/2004
WO WO-2004084993 A1 10/2004
WO WO-2004103455 A2 12/2004
WO WO-2004105870 A1 12/2004
WO WO-2004110549 A2 12/2004
WO WO-2004110550 A2 12/2004
WO WO-2005018739 A1 3/2005
WO WO-2005042091 A1 5/2005
WO WO-2005053788 A1 6/2005
WO WO-2005063332 A1 7/2005
WO WO-2005065771 A1 7/2005
WO WO-2005113066 A1 12/2005
WO WO-2006031331 A1 3/2006
WO WO-2007078410 A1 7/2007
WO WO-2008063396 A1 5/2008
WO WO-2011146393 A2 11/2011

OTHER PUBLICATIONS

U.S. Appl. No. 10/700,368, Final Office Action mailed Oct. 31, 2007, 12 pgs.
U.S. Appl. No. 10/700,368, Non-Final Office Action mailed May 3, 2007, 11 pgs.
U.S. Appl. No. 10/700,368, Non-Final Office Action mailed Jul. 12, 2006, 19 pgs.
U.S. Appl. No. 10/700,368, Non-Final Office Action mailed Feb. 25, 2009, 13 pgs.
U.S. Appl. No. 10/700,368, Non-Final Office Action mailed Mar. 14, 2008, 13 pgs.
U.S. Appl. No. 10/700,368, Notice of Allowance mailed Sep. 15, 2009, 7 pgs.
U.S. Appl. No. 10/700,368, Response filed Jan. 15, 2009 to Final Office Action mailed Oct. 15, 2008, 8 pgs.
U.S. Appl. No. 10/700,368, Response filed Jan. 31, 2008 to Final Office Action mailed Mar. 31, 2007, 8 pgs.
U.S. Appl. No. 10/700,368, Response filed Jun. 16, 2008 to Non-Final Office Action mailed Mar. 14, 2008, 8 pgs.
U.S. Appl. No. 10/700,368, Response filed Jul. 20, 2009 to Non-Final Office Action mailed Feb. 25, 2009, 11 pgs.
U.S. Appl. No. 10/700,368, Response filed Sep. 4, 2007 to Non-Final Office Action mailed May 3, 2007, 8 pgs.

U.S. Appl. No. 10/700,368, Response filed Nov. 13, 2006 to Non-Final office action mailed Jul. 12, 2006, 7 pgs.
U.S. Appl. No. 10/745,920, Final Office Action mailed Jan. 26, 2007, 11 pgs.
U.S. Appl. No. 10/745,920, Non-Final Office Action mailed Jun. 15, 2006, 9 pgs.
U.S. Appl. No. 10/745,920, Non-Final Office Action mailed Oct. 4, 2007, 7 pgs.
U.S. Appl. No. 10/745,920, Notice of Allowance mailed Jul. 29, 2008, 8 pgs.
U.S. Appl. No. 10/745,920, Preliminary Amendment filed Feb. 9, 2004, 5 pgs.
U.S. Appl. No. 10/745,920, Response filed Jan. 4, 2008 to Non-Final Office Action mailed Oct. 4, 2007, 9 pgs.
U.S. Appl. No. 10/745,920, Response filed Apr. 16, 2008 to Restriction Requirement mailed Mar. 17, 2008, 8 pgs.
U.S. Appl. No. 10/745,920, Response filed May 17, 2007 to Final Office Action mailed Jan. 26, 2007, 11 pgs.
U.S. Appl. No. 10/745,920, Response filed Sep. 4, 2007 to Restriction Requirement mailed Aug. 1, 2007, 5 pgs.
U.S. Appl. No. 10/745,920, Response filed Oct. 24, 2006 to Non-Final Office Action mailed Jun. 15, 2006, 11 pgs.
U.S. Appl. No. 10/745,920, Restriction Requirement mailed Mar. 17, 2008, 7 pgs.
U.S. Appl. No. 10/745,920, Restriction Requirement mailed Aug. 1, 2007, 8 pgs.
U.S. Appl. No. 10/745,920, Supplemental Preliminary Amendment filed Apr. 11, 2005, 7 pgs.
U.S. Appl. No. 10/745,920, Supplemental Preliminary Amendment filed Sep. 24, 2004, 7 pgs.
U.S. Appl. No. 10/745,921, Advisory Action mailed Feb. 13, 2007, 5 pgs.
U.S. Appl. No. 10/745,921, Appeal Brief filed Apr. 23, 2007, 38 pgs.
U.S. Appl. No. 10/745,921, Appeal Brief filed Jul. 3, 2007, 37 pgs.
U.S. Appl. No. 10/745,921, Examiner Interview Summary mailed Mar. 24, 2010, 3 pgs.
U.S. Appl. No. 10/745,921, Examiner's Answer mailed Sep. 27, 2007, 17 pgs.
U.S. Appl. No. 10/745,921, Final Office Action mailed Jan. 14, 2010, 16 pgs.
U.S. Appl. No. 10/745,921, Final Office Action mailed Oct. 25, 2006, 11 pgs.
U.S. Appl. No. 10/745,921, Non-Final Office Action mailed Mar. 29, 2006, 10 pgs.
U.S. Appl. No. 10/745,921, Non-Final Office Action mailed Jul. 27, 2009, 15 pgs.
U.S. Appl. No. 10/745,921, Notice of Allowance mailed Sep. 7, 2010, 6 pgs.
U.S. Appl. No. 10/745,921, Preliminary Amendment filed Feb. 9, 2004, 5 pgs.
U.S. Appl. No. 10/745,921, Reply Brief filed Nov. 27, 2007, 31 pgs.
U.S. Appl. No. 10/745,921, Response filed Jan. 25, 2007 to Final Office Action mailed Oct. 25, 2006, 21 pgs.
U.S. Appl. No. 10/745,921, Response filed Feb. 21, 2006 to Restriction Requirement mailed Jan. 19, 2006, 15 pgs.
U.S. Appl. No. 10/745,921, Response file May 6, 2009 to Restriction Requirement mailed Jan. 6, 2009, 12 pgs.
U.S. Appl. No. 10/745,921, Response filed Jun. 14, 2010 to Final Office Action mailed Jan. 14, 2010, 16 pgs.
U.S. Appl. No. 10/745,921, Response file Jul. 31, 2006 to Non-Final Office Action mailed Mar. 29, 2006, 16 pgs.
U.S. Appl. No. 10/745,921, Restriction Requirement mailed Jan. 6, 2009, 9 pgs.
U.S. Appl. No. 10/745,921, Restriction Requirement mailed Jan. 19, 2006, 5 pgs.
U.S. Appl. No. 10/745,921, Supplemental Notice of Allowability mailed Nov. 1, 2010, 4 pgs.
U.S. Appl. No. 10/745,921, Supplemental Preliminary Amendment filed Apr. 25, 2005, 10 pgs.
U.S. Appl. No. 10/745,921, Supplemental Preliminary Amendment filed Sep. 23, 2004, 7 pgs.
U.S. Appl. No. 10/745,925, Final Office Action maile Jan. 11, 2008, 11 pgs.
U.S. Appl. No. 10/745,925, Final Office Action mailed Nov. 24, 2006, 11 pgs.
U.S. Appl. No. 10/745,925, Non-Final Office Action mailed Mar. 28, 2007, 8 pgs.
U.S. Appl. No. 10/745,925, Non-Final Office Action mailed May 1, 2008, 13 pgs.
U.S. Appl. No. 10/745,925, Notice of Allowance mailed Nov. 14, 2008, 6 pgs.
U.S. Appl. No. 10/745,925, Preliminary Amendment filed Feb. 9, 2004, 5 pgs.
U.S. Appl. No. 10/745,925, Response filed Jan. 24, 2007 to Final Office Action mailed Nov. 24, 2006, 14 pgs.
U.S. Appl. No. 10/745,925, Response filed Apr. 11, 2008 to Final Office Action mailed Jan. 11, 2008, 14 pgs.
U.S. Appl. No. 10/745,925, Response filed Jun. 28, 2007 to Non-Final Office Action mailed Mar. 28, 2007, 16 pgs.
U.S. Appl. No. 10/745,925, Response filed Aug. 1, 2008 to Non-Final Office Action mailed May 1, 2008, 11 pgs.
U.S. Appl. No. 10/745,925, Response filed Sep. 20, 2006 to Non-Final Office Action mailed Jun. 20, 2006, 15 pgs.
U.S. Appl. No. 10/745,925, Response filed Oct. 17, 2007 to Restriction Requirement mailed Sep. 18, 2007, 8 pgs.
U.S. Appl. No. 10/745,925, Restriction Requirement mailed Sep. 18, 2007, 5 pgs.
U.S. Appl. No. 10/745,925, Restriction Requirement mailed Jun. 20, 2006, 13 pgs.
U.S. Appl. No. 10/745,925, Supplemental Preliminary Amendment filed Apr. 25, 2005, 10 pgs.
U.S. Appl. No. 10/745,925, Supplemental Preliminary Amendment filed Sep. 24, 2004, 7 pgs.
U.S. Appl. No. 10/746,134, Final Office Action mailed Feb. 21, 2008, 10 pgs.
U.S. Appl. No. 10/746,134, Final Office Action mailed Jul. 10, 2008, 10 pgs.
U.S. Appl. No. 10/746,134, Final Office Action mailed Dec. 26, 2006, 8 pgs.
U.S. Appl. No. 10/746,134, Non Final Office Action mailed May 18, 2007, 12 pgs.
U.S. Appl. No. 10/746,134, Non-Final Office Action mailed Feb. 6, 2009, 10 pgs.
U.S. Appl. No. 10/746,134, Preliminary Amendment filed Feb. 9, 2004, 5 pgs.
U.S. Appl. No. 10/746,134, Preliminary Amendment filed Apr. 25, 2005, 8 pgs.
U.S. Appl. No. 10/746,134, Response filed Feb. 26, 2007 to Final Office Action mailed Dec. 26, 2006, 13 pgs.
U.S. Appl. No. 10/746,134, Response filed Jul. 6, 2009 to Non-Final Office Action mailed Feb. 6, 2009, 16 pgs.
U.S. Appl. No. 10/746,134, Response filed Oct. 5, 2006 to Non-Final Office Action mailed May 5, 2006, 16 pgs.
U.S. Appl. No. 10/746,134, Response filed Nov. 19, 2007 to Non-Final Office Action mailed May 18, 2007, 14 pgs.
U.S. Appl. No. 10/746,134, Response filed Dec. 10, 2008 to Final Office Action mailed Jul. 10, 2008, 11 pgs.
U.S. Appl. No. 10/746,134, Supplemental Notice of Allowability mailed Aug. 31, 2009, 5 pgs.
U.S. Appl. No. 10/746,134, Supplemental Preliminary Amendment filed Sep. 23, 2004, 7 pgs.
U.S. Appl. No. 10/746,134, Supplemental Preliminary Amendment filed Nov. 30, 2004, 3 pgs.
U.S. Appl. No. 10/746,135, Appeal Brief mailed May 10, 2010, 43 pgs.
U.S. Appl. No. 10/746,135, Decision on Pre-Appeal Brief Request mailed Mar. 10, 2010, 2 pgs.
U.S. Appl. No. 10/746,135, Examiner Interview Summary mailed Feb. 6, 2009, 8 pgs.
U.S. Appl. No. 10/746,135, Examiner's Answer to Appeal Brief mailed Jul. 22, 2010, 17 pgs.
U.S. Appl. No. 10/746,135, Final Office Action mailed Mar. 18, 2008, 16 pgs.
U.S. Appl. No. 10/746,135, Final Office Action mailed Jul. 22, 2009, 14 pgs.

U.S. Appl. No. 10/746,135, Non-Final Office Action mailed Feb. 12, 2007, 21 pgs.
U.S. Appl. No. 10/746,135, Non-Final Office Action mailed Jul. 19, 2007, 27 pgs.
U.S. Appl. No. 10/746,135, Non-Final Office Action mailed Aug. 1, 2006, 33 pgs.
U.S. Appl. No. 10/746,135, Non-Final Office Action mailed Sep. 30, 2008, 18 pgs.
U.S. Appl. No. 10/746,135, Pre-Appeal Brief Request filed Dec. 21, 2009, 5 pgs.
U.S. Appl. No. 10/746,135, Preliminary Amendment filed Feb. 9, 2004, 5 pgs.
U.S. Appl. No. 10/746,135, Reply Brief filed Sep. 22, 2010, 9 pgs.
U.S. Appl. No. 10/746,135, Response filed Mar. 30, 2009 to Non-Final Office Action mailed Sep. 30, 2008, 26 pgs.
U.S. Appl. No. 10/746,135, Response filed May 2, 2007 to Non-Final Office Action mailed Feb. 12, 2007, 19 pgs.
U.S. Appl. No. 10/746,135, Response filed Jul. 7, 2006 to Restriction Requirement mailed Jun. 9, 2006, 9 pgs.
U.S. Appl. No. 10/746,135, Response filed Jul. 17, 2008 to Final Office Action mailed Mar. 18, 2008, 20 pgs.
U.S. Appl. No. 10/746,135, Response filed Nov. 21, 2006 to Non-Final Office Action mailed Aug. 1, 2006, 17 pgs.
U.S. Appl. No. 10/746,135, Response filed Dec. 19, 2007 to Non-Final Office Action mailed Jul. 19, 2007, 22 pgs.
U.S. Appl. No. 10/746,135, Restriction Requirement mailed Jun. 9, 2006, 5 pgs.
U.S. Appl. No. 10/746,135, Supplemental Preliminary Amendment filed Apr. 11, 2005, 9 pgs.
U.S. Appl. No. 10/746,135, Supplemental Preliminary Amendment filed Sep. 23, 2004, 7 pgs.
U.S. Appl. No. 10/746,844, Advisory Action mailed Oct. 31, 2008, 3 pgs.
U.S. Appl. No. 10/746,844, Final Office Action mailed Aug. 13, 2008, 8 pgs.
U.S. Appl. No. 10/746,844, Final Office Action mailed Aug. 17, 2009, 9 pgs.
U.S. Appl. No. 10/746,844, Final Office Action mailed Oct. 6, 2006, 10 pgs.
U.S. Appl. No. 10/746,844, Non-Final Office Action mailed Jan. 31, 2008, 8 pgs.
U.S. Appl. No. 10/746,844, Non-Final Office Action mailed Apr. 6, 2006, 10 pgs.
U.S. Appl. No. 10/746,844, Non-Final Office Action mailed Feb. 10, 2009, 9 pgs.
U.S. Appl. No. 10/746,844, Non-Final Office Action mailed Apr. 3, 2007, 8 pgs.
U.S. Appl. No. 10/746,844, Notice of Allowance mailed Dec. 18, 2009, 5 pgs.
U.S. Appl. No. 10/746,844, Preliminary Amendment filed Feb. 9, 2004, 5 pgs.
U.S. Appl. No. 10/746,844, Response filed Jan. 8, 2007 to Final Office Action mailed Oct. 6, 2006, 12 pgs.
U.S. Appl. No. 10/746,844, Response filed Apr. 30, 2008 to Non-Final Office Action mailed Jan. 31, 2008, 14 pgs.
U.S. Appl. No. 10/746,844, Response filed May 11, 2009 to Non-Final Office Action mailed Feb. 10, 2009, 20 pgs.
U.S. Appl. No. 10/746,844, Response filed Jul. 6, 2006 to Non-Final Office Action mailed Apr. 6, 2006, 15 pgs.
U.S. Appl. No. 10/746,844, Response filed Jul. 30, 2007 to Non-Final Office Action mailed Apr. 3, 2007, 12 pgs.
U.S. Appl. No. 10/746,844, Response filed Oct. 14, 2008 to Final Office Action mailed Aug. 13, 2008, 15 pgs.
U.S. Appl. No. 10/746,844, Response filed Oct. 19, 2009 to Final Office Action mailed Aug. 17, 2009, 9 pgs.
U.S. Appl. No. 10/746,844, Response filed Nov. 16, 2007 to Restriction Requirement mailed Oct. 17, 2007, 17 pgs.
U.S. Appl. No. 10/746,844, Response filed Dec. 15, 2008 to Final Office Action mailed Aug. 13, 2008, 15 pgs.
U.S. Appl. No. 10/746,844, Restriction Requirement mailed Oct. 17, 2007, 9 pgs.
U.S. Appl. No. 10/746,844, Supplemental Preliminary Amendment filed Apr. 11, 2005, 9 pgs.
U.S. Appl. No. 10/746,844, Supplemental Preliminary Amendment filed Sep. 24, 2004, 7 pgs.
U.S. Appl. No. 10/746,845, Advisory Action mailed Oct. 12, 2006, 3 pgs.
U.S. Appl. No. 10/746,845, Final Office Action mailed Aug. 3, 2006, 14 pgs.
U.S. Appl. No. 10/746,845, Final Office Action mailed Aug. 8, 2007, 11 pgs.
U.S. Appl. No. 10/746,845, Non-Final Office Action mailed Jan. 19, 2006, 12 pgs.
U.S. Appl. No. 10/746,845, Non-Final Office Action mailed Feb. 20, 2007, 17 pgs.
U.S. Appl. No. 10/746,845, Non-Final Office Action mailed Jan. 16, 2008, 10 pgs.
U.S. Appl. No. 10/746,845, Notice of Allowance mailed Sep. 23, 2008, 4 pgs.
U.S. Appl. No. 10/746,845, Preliminary Amendment filed Feb. 9, 2004, 5 pgs.
U.S. Appl. No. 10/746,845, Response filed May 15, 2008 to Non-Final Office Action mailed Jan. 16, 2008, 18 pgs.
U.S. Appl. No. 10/746,845, Response filed May 19, 2006 to Non-Final Office Action mailed Jan. 19, 2006, 14 pgs.
U.S. Appl. No. 10/746,845, Response filed May 21, 2007 to Non-Final Office Action mailed Feb. 20, 2007, 17 pgs.
U.S. Appl. No. 10/746,845, Response filed Oct. 3, 2006 to Final Office Action mailed Aug. 3, 2006, 15 pgs.
U.S. Appl. No. 10/746,845, Response filed Oct. 29, 2007 to Final Office Action mailed Aug. 8, 2007, 15 pgs.
U.S. Appl. No. 10/746,845, Supplemental Preliminary Amendment filed Apr. 11, 2005, 9 pgs.
U.S. Appl. No. 10/746,845, Supplemental Preliminary Amendment filed Jun. 11, 2004, 3 pgs.
U.S. Appl. No. 10/746,845, Supplemental Preliminary Amendment filed Sep. 24, 2004, 7 pgs.
U.S. Appl. No. 10/746,846, Final Office Action mailed Jan. 23, 2008, 18 pgs.
U.S. Appl. No. 10/746,846, Final Office Action mailed Feb. 12, 2007, 17 pgs.
U.S. Appl. No. 10/746,846, Non-Final Office Action mailed Apr. 26, 2007, 18 pgs.
U.S. Appl. No. 10/746,846, Non-Final Office Action mailed Jul. 25, 2006, 15 pgs.
U.S. Appl. No. 10/746,846, Preliminary Amendment filed Feb. 9, 2004, 5 pgs.
U.S. Appl. No. 10/746,846, Response filed Apr. 17, 2007 to Final Office Action mailed Feb. 12, 2007, 16 pgs.
U.S. Appl. No. 10/746,846, Response filed Jul. 7, 2006 to Restriction Requirement mailed Jun. 9, 2006, 13 pgs.
U.S. Appl. No. 10/746,846, Response filed Oct. 26, 2007 to Non-Final Office Action mailed Apr. 26, 2007, 11 pgs.
U.S. Appl. No. 10/746,846, Response filed Nov. 9, 2006 to Non-Final Office Action mailed Jul. 25, 2006, 17 pgs.
U.S. Appl. No. 10/746,846, Restriction Requirement mailed Jun. 9, 2006, 7 pgs.
U.S. Appl. No. 10/746,846, Supplemental Preliminary Amendment filed Apr. 25, 2005, 13 pgs.
U.S. Appl. No. 10/746,846, Supplemental Preliminary Amendment filed Sep. 23, 2004, 7 pgs.
U.S. Appl. No. 10/746,847, Examiner Interview Summary mailed Jun. 16, 2009, 9 pgs.
U.S. Appl. No. 10/746,847, Final Office Action mailed Feb. 25, 2008, 10 pgs.
U.S. Appl. No. 10/746,847, Final Office Action mailed Oct. 1, 2009, 10 pgs.
U.S. Appl. No. 10/746,847, Non-Final Office Action mailed Sep. 13, 2006, 14 pgs.
U.S. Appl. No. 10/746,847, Non-Final Office Action mailed Mar. 2, 2007, 17 pgs.
U.S. Appl. No. 10/746,847, Non-Final Office Action mailed Aug. 28, 2007, 18 pgs.
U.S. Appl. No. 10/746,847, Non-Final Office Action mailed Sep. 30, 2008, 13 pgs.

U.S. Appl. No. 10/746,847, Preliminary Amendment filed Feb. 9, 2004, 5 pgs.
U.S. Appl. No. 10/746,847, Response filed Feb. 26, 2009 to Non-Final Office Action mailed Sep. 30, 2008, 10 pgs.
U.S. Appl. No. 10/746,847, Response filed May 30, 2007 to Non-Final Office Action mailed Mar. 2, 2007, 14 pgs.
U.S. Appl. No. 10/746,847, Response filed Jul. 14, 2008 to Final Office Action mailed Feb. 25, 2008, 11 pgs.
U.S. Appl. No. 10/746,847, Response filed Aug. 14, 2006 to Non-Final Office Action mailed Jul. 14, 2006, 9 pgs.
U.S. Appl. No. 10/746,847, Response filed Nov. 28, 2007 to Non-Final Office Action mailed Aug. 28, 2007, 13 pgs.
U.S. Appl. No. 10/746,847, Response filed Dec. 13, 2006 to Non-Final Office Action mailed Sep. 13, 2006, 13 pgs.
U.S. Appl. No. 10/746,847, Restriction Requirement mailed Jul. 14, 2006 , 8 pgs.
U.S. Appl. No. 10/746,847, Supplemental Preliminary Amendment filed Apr. 25, 2005, 8 pgs.
U.S. Appl. No. 10/746,847, Supplemental Preliminary Amendment filed Sep. 23, 2004, 7 pgs.
U.S. Appl. No. 10/746,852, Advisory Action mailed Jun. 26, 2008, 3 pgs.
U.S. Appl. No. 10/746,852, Appeal Brief filed Dec. 22, 2008, 26 pgs.
U.S. Appl. No. 10/746,852, Decision on Pre-Appeal Brief mailed Aug. 22, 2008, 2 pgs.
U.S. Appl. No. 10/746,852, Examiner's Answer mailed Mar. 13, 2009, 17 pgs.
U.S. Appl. No. 10/746,852, Final Office Action mailed Mar. 27, 2008, 15 pgs.
U.S. Appl. No. 10/746,852, Final Office Action mailed Aug. 26, 2008, 14 pgs.
U.S. Appl. No. 10/746,852, Non-Final Office Action mailed Apr. 6, 2006, 12 pgs.
U.S. Appl. No. 10/746,852, Non-Final Office Action mailed Apr. 17, 2007, 16 pgs.
U.S. Appl. No. 10/746,852, Non-Final Office Action mailed Oct. 25, 2006, 15 pgs.
U.S. Appl. No. 10/746,852, Non-Final Office Action mailed Oct. 9, 2007, 15 pgs.
U.S. Appl. No. 10/746,852, Pre-Appeal Brief Request filed Jul. 18, 2008, 5 pgs.
U.S. Appl. No. 10/746,852, Response filed Jan. 9, 2008 to Non-Final Office Action mailed Oct. 9, 2007, 15 pgs.
U.S. Appl. No. 10/746,852, Response filed Jan. 25, 2007 to Non-Final Office Action mailed Oct. 25, 2006, 16 pgs.
U.S. Appl. No. 10/746,852, Response filed May 27, 2008 to Final Office Action mailed Mar. 27, 2008, 15 pgs.
U.S. Appl. No. 10/746,852, Response filed Jul. 17, 2007 to Non-Final Office Action mailed Apr. 17, 2007, 12 pgs.
U.S. Appl. No. 10/746,852, Response filed Aug. 7, 2006 to Non-Final Office Action mailed Apr. 6, 2006, 14 pgs.
U.S. Appl. No. 10/746,861, Advisory Action mailed Jan. 31, 2007, 3 pgs.
U.S. Appl. No. 10/746,861, Advisory Action mailed Jul. 18, 2008, 3 pgs.
U.S. Appl. No. 10/746,861, Advisory Action mailed Nov. 12, 2010, 3 pgs.
U.S. Appl. No. 10/746,861, Decision on Pre-Appeal Brief mailed Nov. 21, 2008, 2 pgs.
U.S. Appl. No. 10/746,861, Examiner Interview Summary mailed Mar. 26, 2010, 3 pgs.
U.S. Appl. No. 10/746,861, Final Office Action mailed Apr. 21, 2008, 13 pgs.
U.S. Appl. No. 10/746,861, Final Office Action mailed Jul. 7, 2010, 12 pgs.
U.S. Appl. No. 10/746,861, Final Office Action mailed Oct. 24, 2006, 20 pgs.
U.S. Appl. No. 10/746,861, Non-Final Office Action mailed Apr. 6, 2006, 22 pgs.
U.S. Appl. No. 10/746,861, Non-Final Office Action mailed Jul. 12, 2007, 21 pgs.
U.S. Appl. No. 10/746,861, Non-Final Office Action mailed Feb. 2, 2009, 9 pgs.
U.S. Appl. No. 10/746,861, Non-Final Office Action mailed Nov. 24, 2009, 8 pgs.
U.S. Appl. No. 10/746,861, Notice of Allowance mailed May 13, 2011, 7 pgs.
U.S. Appl. No. 10/746,861, Notice of Appeal filed Apr. 24, 2007, 3 pgs.
U.S. Appl. No. 10/746,861, Pre-Appeal Brief Request filed Oct. 21, 2008, 5 pgs.
U.S. Appl. No. 10/746,861, Response filed Jan. 24, 2007 to Final Office Action mailed Oct. 24, 2006, 12 pgs.
U.S. Appl. No. 10/746,861, Response filed Mar. 24, 2010 to Non-Final Office Action mailed Nov. 24, 2009, 14 pgs.
U.S. Appl. No. 10/746,861, Response filed Jun. 25, 2007 to Advisory Action mailed Jan. 31, 2007, 12 pgs.
U.S. Appl. No. 10/746,861, Response filed Jul. 1, 2009 to Non-Final Office Action mailed Feb. 2, 2009, 9 pgs.
U.S. Appl. No. 10/746,861, Response filed Aug. 7, 2006 to Non-Final Office Action mailed Apr. 6, 2006, 13 pgs.
U.S. Appl. No. 10/746,861, Response filed Sep. 7, 2010 to Final Office Action mailed Jul. 7, 2010, 13 pgs.
U.S. Appl. No. 10/746,861, Response filed Dec. 12, 2007 to Non-Final Office Action mailed Jul. 12, 2007, 13 pgs.
U.S. Appl. No. 10/746,861, Response filed Jun. 23, 2008 to Final Office Action mailed Apr. 21, 2008, 12 pgs.
U.S. Appl. No. 10/939,544, Examiner Interview Summary mailed Sep. 3, 2008, 14 pgs.
U.S. Appl. No. 10/939,544, Examiner Interview Summary mailed Nov. 6, 2006, 2 pgs.
U.S. Appl. No. 10/939,544, Final Office Action mailed Mar. 5, 2009, 14 pgs.
U.S. Appl. No. 10/939,544, Final Office Action mailed Apr. 27, 2007, 10 pgs.
U.S. Appl. No. 10/939,544, Non Final Office Action mailed Oct. 27, 2006, 18 pgs.
U.S. Appl. No. 10/939,544, Non-Final Office Action mailed May 12, 2008, 14 pgs.
U.S. Appl. No. 10/939,544, Non-Final Office Action mailed Oct. 12, 2007, 14 pgs.
U.S. Appl. No. 10/939,544, Notice of Allowance mailed Sep. 3, 2009, 12 pgs.
U.S. Appl. No. 10/939,544, Preliminary Amendment filed Apr. 25, 2005, 11 pgs.
U.S. Appl. No. 10/939,544, Response filed Jan. 29, 2007 to Non-Final Office Action mailed Oct. 27, 2006, 14 pgs.
U.S. Appl. No. 10/939,544, Response filed Feb. 12, 2008 to Non-Final Office Action mailed Oct. 12, 2007, 17 pgs.
U.S. Appl. No. 10/939,544, Response filed Aug. 5, 2009 to Final Office Action mailed Mar. 5, 2009, 16 pgs.
U.S. Appl. No. 10/939,544, Response filed Sep. 3, 2008 to Non-Final Office Action mailed May 12, 2008, 17 pgs.
U.S. Appl. No. 10/939,544, Response filed Sep. 27, 2007 to Final Office Action mailed Apr. 27, 2007, 12 pgs.
U.S. Appl. No. 11/078,460, Final Office Action mailed Jul. 30, 2008, 7 pgs.
U.S. Appl. No. 11/078,460, Notice of Allowance mailed May 1, 2009, 4 pgs.
U.S. Appl. No. 11/078,460, Notice of Allowance mailed Nov. 10, 2008, 6 pgs.
U.S. Appl. No. 11/078,460, Response filed Apr. 18, 2008 to Non-Final Office Action mailed Jan. 18, 2008, 14 pgs.
U.S. Appl. No. 11/078,460, Response filed Sep. 29, 2008 to Final Office Action mailed Jul. 30, 2008, 11 pgs.
U.S. Appl. No. 11/078,460, Non-Final Office Action mailed Jan. 18, 2008, 6 pgs.
U.S. Appl. No. 11/126,097, Final Office Action mailed Feb. 18, 2009, 10 pgs.
U.S. Appl. No. 11/126,097, Notice of Allowance mailed Dec. 7, 2009, 7 pgs.
U.S. Appl. No. 11/126,097, Response and Preliminary Amendment filed Apr. 28, 2008 to Restriction Requirement mailed Mar. 26, 2008, 13 pgs.
U.S. Appl. No. 11/126,097, Response filed Jun. 15, 2009 to Restriction Requirement mailed May 14, 2009, 8 pgs.

U.S. Appl. No. 11/126,097, Response filed Nov. 19, 2008 to Non-Final Office Action mailed Aug. 19, 2008, 11 pgs.
U.S. Appl. No. 11/126,097, Response filed May 4, 2009 to Final Office Action mailed Feb. 18, 2009, 11 pgs.
U.S. Appl. No. 11/126,097, Restriction Requirement mailed May 14, 2009, 7 pgs.
U.S. Appl. No. 11/276,107, Final Office Action mailed Jan. 27, 2010, 9 pgs.
U.S. Appl. No. 11/276,107, Non-Final Office Action mailed Jun. 21, 2010, 8 pgs.
U.S. Appl. No. 11/276,107, Non-Final Office Action mailed Jun. 26, 2009, 30 pgs.
U.S. Appl. No. 11/276,107, Response filed Mar. 23, 2009 to Restriction Requirement mailed Feb. 20, 2009, 9 pgs.
U.S. Appl. No. 11/276,107, Response filed Apr. 26, 2010 to Final Office Action mailed Jan. 27, 2010, 10 pgs.
U.S. Appl. No. 11/276,107, Response filed Sep. 7, 2010 to Non-Final Office Action mailed Jun. 21, 2010, 11 pgs.
U.S. Appl. No. 11/276,107, Response filed Sep. 28, 2009 to Non-Final Office Action mailed Jun. 26, 2009, 10 pgs.
U.S. Appl. No. 11/276,107, Response filed Nov. 26, 2008 to Restriction Requirement mailed Oct. 31, 2008, 10 pgs.
U.S. Appl. No. 11/276,107, Restriction Requirement mailed Oct. 31, 2008, 5 pgs.
U.S. Appl. No. 11/276,107, Restriction Requirement mailed Feb. 20, 2009, 6 pgs.
U.S. Appl. No. 11/312,178, Non-Final Office Action mailed May 14, 2008, 6 pgs.
U.S. Appl. No. 11/312,178, Notice of Allowance mailed Apr. 3, 2009, 6 pgs.
U.S. Appl. No. 11/312,178, Notice of Allowance mailed Nov. 14, 2008, 6 pgs.
U.S. Appl. No. 11/312,178, Preliminary Amendment filed Mar. 14, 2006, 7 pgs.
U.S. Appl. No. 11/312,178, Response filed Aug. 14, 2008 to Non-Final Office Action mailed May 14, 2008, 14 pgs.
U.S. Appl. No. 11/428,131, Substitute Preliminary Statement dated Jul. 5, 2006, 2 pgs.
U.S. Appl. No. 11/482,225, Preliminary Statement filed Oct. 31, 2006, 2 pgs.
U.S. Appl. No. 11/482,264, Preliminary Statement filed Oct. 30, 2006, 1 pg.
U.S. Appl. No. 11/482,357, Non-Final Office Action mailed Jul. 17, 2009, 12 pgs.
U.S. Appl. No. 11/482,357, Notice of Allowance mailed Mar. 25, 2010, 4 pgs.
U.S. Appl. No. 11/482,357, Preliminary Statement mailed Oct. 30, 2006, 3 pgs.
U.S. Appl. No. 11/482,357, Response filed Dec. 17, 2009 to Non-Final Office Action mailed Jul. 17, 2009, 13 pgs.
U.S. Appl. No. 11/482,453, Preliminary Statement filed Oct. 31, 2006, 3 pgs.
U.S. Appl. No. 11/482,505, Preliminary Amendment Oct. 31, 2006, 2 pgs.
U.S. Appl. No. 11/482,563, Preliminary StatementOct. 31, 2006, 2 pgs.
U.S. Appl. No. 11/482,635, Preliminary Statement Oct. 31, 2006, 2 pgs.
U.S. Appl. No. 11/482,662, Preliminary Statement mailed Oct. 31, 2006, 3 pgs.
U.S. Appl. No. 11/558,083, 1.312 Amendment filed Jul. 8, 2010, 10 pgs.
U.S. Appl. No. 11/558,083, Non-Final Office Action mailed Jun. 26, 2009, 17 pgs.
U.S. Appl. No. 11/558,083, Preliminary Amendment filed Nov. 13, 2006, 3 pgs.
U.S. Appl. No. 11/558,083, Preliminary Amendment mailed Nov. 13, 2006, 3 pgs.
U.S. Appl. No. 11/558,083, Response to 312 Amendment mailed Jul. 21, 2010, 2 pgs.
U.S. Appl. No. 11/558,083, Response filed Dec. 22, 2009 to Non-Final Office Action mailed Jun. 26, 2009, 15 pgs.
U.S. Appl. No. 11/621,194, Final Office Action mailed May 19, 2010, 8 pgs.
U.S. Appl. No. 11/621,194, Non-Final Office Action mailed Oct. 1, 2009, 22 pgs.
U.S. Appl. No. 11/621,194, Response filed Aug. 19, 2010 to Final Office Action mailed May 19, 2010, 8 pgs.
U.S. Appl. No. 11/933,252, Preliminary Statement filed Oct. 31, 2007, 3 pgs.
U.S. Appl. No. 11/933,268, Preliminary Statement filed Oct. 31, 2007, 2 pgs.
U.S. Appl. No. 12/126,182, Non-Final Office Action mailed Jul. 23, 2010, 9 pgs.
U.S. Appl. No. 12/126,182, Notice of Allowance mailed Apr. 18, 2011, 12 pgs.
U.S. Appl. No. 12/126,182, Response filed Oct. 25, 2010 to Non-Final Office Action mailed Jul. 23, 2010, 12 pgs.
U.S. Appl. No. 12/257,079, Non-Final Office Action mailed Oct. 1, 2010, 10 pgs.
U.S. Appl. No. 12/257,079, Response filed Mar. 1, 2011 to Non-Final Office Action mailed Oct. 1, 2010, 9 pgs.
U.S. Appl. No. 12/257,079, Response filed Sep. 7, 2010 to Restriction Requirement mailed Aug. 5, 2010, 9 pgs.
U.S. Appl. No. 12/257,079, Restriction Requirement mailed Aug. 5, 2010, 5 pgs.
U.S. Appl. No. 12/321,949, Final Office Action mailed Dec. 16, 2010, 8 pgs.
U.S. Appl. No. 12/321,949, Non-Final Office Action mailed Jul. 29, 2010, 8 pgs.
U.S. Appl. No. 12/321,949, Response filed Mar. 9, 2011 to Final Office Action mailed Dec. 16, 2010, 8 pgs.
U.S. Appl. No. 12/321,949, Response filed Jun. 3, 2010 to Restriction Requirement mailed May 3, 2010, 11 pgs.
U.S. Appl. No. 12/321,949, Response filed Oct. 29, 2010 to Non-Final Office Action mailed Jul. 29, 2010, 9 pgs.
U.S. Appl. No. 12/321,949, Restriction Requirement mailed May 3, 2010, 7 pgs.
U.S. Appl. No. 12/368,842, Non-Final Office Action mailed Dec. 28, 2010, 10 pgs.
U.S. Appl. No. 12/368,842, Response filed Nov. 1, 2010 to Restriction Requirement mailed Sep. 30, 2010, 9 pgs.
U.S. Appl. No. 12/368,842, Response filed Mar. 28, 2011 to Non-Final Office Action mailed Dec. 28, 2010, 10 pgs.
U.S. Appl. No. 12/368,842, Restriction Requirement mailed Sep. 30, 2010, 6 pgs.
U.S. Appl. No. 12/693,660, Final Office Action mailed Apr. 21, 2011, 10 pgs.
U.S. Appl. No. 12/693,660, Non-Final Office Action mailed Oct. 28, 2010, 8 pgs.
U.S. Appl. No. 12/693,660, Response filed Feb. 28, 2011 to Non-Final Office Action mailed Oct. 28, 2010, 9 pgs.
U.S. Appl. No. 12/693,660, Response filed Sep. 2, 2010 to Restriction Requirement mailed Aug. 2, 2010, 7 pgs.
U.S. Appl. No. 12/693,660, Restriction Requirement mailed Aug. 2, 2010, 8 pgs.
U.S. Appl. No. 12/749,939, Non-Final Office Action mailed Mar. 21, 2011, 14 pgs.
European Application Serial No. 05787559.3, Response filed Jul. 23, 2009 to Communication mailed Jan. 29, 2009, 12 pgs.
European Application Serial No. 06827323.4, Communication mailed Jun. 2, 2009, 2 pgs.
European Application Serial No. 06827323.4, Communication mailed Nov. 12, 2008., 3 pgs.
European Application Serial No. 06827323.4, Response filed Apr. 24, 2009 to Communication mailed Nov. 12, 2008, 6 pgs.
European Application Serial No. 06827323.4, Summons to Attend Oral Proceedings mailed May 19, 2010, 3 pgs.
European Application Serial No. 06827323.4, Written Submissions filed Sep. 23, 2010, 4 pgs.
European Application Serial No. 07861710.7, Office Action mailed Aug. 23, 2010, 3 pgs.
European Application Serial No. 07861710.7, Response filed Feb. 28, 2011 to Non Final Office Action mailed Aug. 23, 2010, 15 pgs.

European Application Serial No. 5787559.3, Office Action mailed Jan. 29, 2009, 10 pgs.
International Application Serial No. PCT/US2004/036606, Written Opinion dated Mar. 10, 2005, 5 pgs.
International Application Serial No. PCT/US2004/043691, International Search Report mailed Mar. 22, 2005, 3 pgs.
International Application Serial No. PCT/US2004/043691, Written Opinion mailed Mar. 22, 2005, 7 pgs.
International Application Serial No. PCT/US2006/042727, International Search Report and Written Opinion mailed Apr. 23, 2007, 16 pgs.
International Application Serial No. PCT/US2006/042727, Written Opinion mailed Apr. 23, 2007, 9 pgs.
International Application Serial No. PCT/US2007/023288, International Search Report and Written Opinion mailed Apr. 23, 2008, 13 pgs.
Japanese Application Serial No. 2006-547356, Office Action mailed Jul. 6, 2010, (w/ English translation), 7 pgs.
Japanese Application Serial No. 2006-547356, Office Action Response filed Oct. 5, 2010, (w/ English Translation of Amended Claims), 68 pgs.
Japanese Application Serial No. 2006-547356, Response filed Apr. 20, 2011 to Office Action mailed Feb. 1, 2011, 11 pgs.
Japanese Application Serial No. 2006-547356, Office Action mailed Feb. 1, 2011, (w/ English Translation), 15 pgs.
Japanese Application Serial No. 2006-547492, Notice of Allowance dated Oct. 29, 2010, (w/ English Translation), 2 pgs.
Japanese Application Serial No. 2006-547492, Office Action mailed Jun. 8, 2010, (w/ English Translation), 5 pgs.
Japanese Application Serial No. 2006-547492, Response filed Oct. 6, 2010 to Office Action dated Jun. 8, 2010, (w/ English Translation of Amended Claims), 14 pgs.
Abraham, W T, "Cardiac Resynchronization in Chronic Heart Failure", New England Journal of Medicine, 346(24), (Jul. 13, 2002), 1845-1853.
Andersen, H, et al., "Long-term follow-up of patients from a randomised trial of atrial versus ventricular pacing for sick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.
Bevan, J A, et al., "Postganglionic sympathetic delay in vascular smooth muscle", Journal of Pharmacology & Experimental Therapeutics, 152(2), (May 1966), 221-30.
Bevan, J A, et al., "Sympathetic nerve-free vascular muscle", Journal of Pharmacology & Experimental Therapeutics, 157(1), (Jul. 1967), 117-24.
Bilgutay, A M, et al., "A new concept in the treatment of hypertension utilizing an implantable electronic device: "Baropacer"", Trans Am Soc Artif Intern Organs., 10, (1964), 387-395.
Bilgutay, A M, et al., "Vagal tuning for the control of supraventricular arrhythmias", Surgical Forum, 16, (1965), 151-3.
Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.
Borst, C, et al., "Optimal frequency of carotid sinus nerve stimulation in treatment of angina pectoris", Cardiovascular Research, 8(5), (Sep. 1974), 674-80.
Braunwald, E, et al., "Carotid sinus nerve stimulation in the treatment of angina pectoris and supraventricular tachycardia", California Medicine, 112(3), (Mar. 1970), 41-50.
Braunwald, E, et al., "Relief of angina pectoris by electrical stimulation of the carotid-sinus nerves", New England Journal of Medicine, 277(24), (Dec. 14, 1967), 1278-83.
Chapleau, M W, "Neuro-cardiovascular regulation: from molecules to man. Introduction.", Annals of the New York Academy of Sciences, 940, (Jun. 2001), xiii-xxii.
Chapleau, M W, et al., "Pulsatile activation of baroreceptors causes central facilitation of baroreflex", American Journal of Physiology, 256(6 Pt 2), (Jun. 1989), H1735-41.
Chapleau, M. W., et al., "Contrasting effects of static and pulsatile pressure on carotid baroreceptor activity in dogs", Circulation, vol. 61, No. 5, (Nov. 1987), 648-658.
Chavan, Abhi, et al., "Implantable and Rechargeable Neural Stimulator", U.S. Appl. No. 11/256,907, filed Oct. 24, 2005, 35 pgs.
Coleridge, J C, et al., "Relationship between pulmonary arterial pressure and impulse activity in pulmonary arterial baroreceptor fibres", Journal of Physiology, 158, (Sep. 1961), 197-205.
Coleridge, J C, et al., "The distribution, connexions and histology of baroreceptors in the pulmonary artery, with some observations on the sensory innervation of the ductus arteriosus", Journal of Physiology, 156, (May 1961), 591-602.
Coleridge, J. C, et al., "Reflex effects of stimulating baroreceptors in the pulmonary artery", J. Physiol, 166, (1963), 197-210.
Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.
Courtice, G P, et al., "Effect of frequency and impulse pattern on the non-cholinergic cardiac response to vagal stimulation in the toad, *Bufo marinus*", Journal of the Autonomic Nervous System, 48(3), (Aug. 1994), 267-72.
Dart, Jr., C H, et al., "Carotid sinus nerve stimulation treatment of angina refractory to other surgical procedures", Annals of Thoracic Surgery, 11(4), (Apr. 1971), 348-59.
De Landsheere, D, et al., "Effect of spinal cord stimulation on regional myocardial perfusion assessed by positron emission tomography", American Journal of Cardiology, 69(14), (May 1, 1992), 1143-9.
Dickerson, L W, "Parasympathetic neurons in the cranial medial ventricular fat pad on the dog heart selectively decrease ventricular contractility", Journal of the Autonomic Nervous System, 70(1-2), (May 28, 1998), 129-41.
Diedrich, A, "Analysis of raw microneurographic recordings based on wavelet de-noising technique and classification algorithm: wavelet analysis in microneurography", IEEE Transactions on Biomedical Engineering, 50(1), (Jan. 2003), 41-50.
Dunning, A. J., "Electrostimulation of the Carotid Sinus Nerve in Angina Pectoris", University Department of Medicine, Binnengasthuis, Amsterdam; Printed by Royal VanGorcum, Assen, Netherlands, (1971), 1-92.
Epstein, S. E., et al., "Treatment of angina pectoris by electrical stimulation of the carotid-sinus nerves", New England Journal of Medicine, 280(18), (May 1, 1969), 971-978.
Farrehi, C, "Stimulation of the carotid sinus nerve in treatment of angina pectoris", American Heart Journal, 80(6), (Dec. 1970), 759-65.
Feliciano, L, et al., "Vagal nerve stimulation releases vasoactive intestinal peptide which significantly increases coronary artery blood flow", Cardiovascular Research, 40(1), (Oct. 1998), 45-55.
Fromer, M, et al., "Ultrarapid subthreshold stimulation for termination of atrioventricular node reentrant tachycardia", Journal of the American College of Cardiology, 20(4), (Oct. 1992), 879-83.
Gatti, P J, et al., "Vagal control of left ventricular contractility is selectively mediated by a cranioventricular intracardiac ganglion in the cat", J Auton Nery Syst., 66(3), (Oct. 13, 1997), 138-44.
Grassi, Guido, et al., "Baroreflex and non-baroreflex modulation of vagal cardiac control after myocardial infarction", Am J Cardiol., 84(5), (Sep. 1, 1999), 525-529.
Griffith, Lawrence S.C., et al., "Electrical Stimulation of the Carotid Sinus Nerve in Normotensive and Renal Hypertensive Dogs", Circulation, 28, (Jul.-Dec. 1963), 730.
Heil, Jr., Ronald W., et al., "Barorelflex Stimulation System to Reduce Hypertension", U.S. Appl. No. 10/746,134, filed Dec. 24, 2003, 78 pgs.
Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.
Henning, R J, et al., "Vagal nerve stimulation increases right ventricular contraction and relaxation and heart rate", Cardiovascular Research, 32(5), (Nov. 1996), 846-53.

Henning, R J, et al., "Vagal stimulation attenuates sympathetic enhancement of left ventricular function", American Journal of Physiology, 258(5 Pt 2), (May 1990), H1470-5.
Holder, L K, "Treatment of refractory partial seizures: preliminary results of a controlled study", Pacing & Clinical Electrophysiology, 15(10 Pt 2), (Oct. 1992), 1557-71.
Hood Jr., W B, et al., "Asynchronous contraction due to late systolic bulging at left ventricular pacing sites", American Journal of Physiology, 217(1), (Jul. 1969), 215-21.
Ishise, H, et al., "Time course of sympathovagal imbalance and left ventricular dysfunction in conscious dogs with heart failure", Journal of Applied Physiology, 84(4), (Apr. 1998), 1234-41.
Janes, R. D., et al., "Anatomy of human extrinsic cardiac nerves and ganglia.", Am J Cardiol., 57(4), (Feb. 1, 1986), 299-309.
Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1999;83(4):642, (Oct. 15, 1998), 921-6.
Kandel, Eric R, et al., "Part VII: Arousal, Emotion, and Behavioral Homeostasis", In: Principles of Neural Science, New York : McGraw-Hill, Health Professions Division, (2000), 966-969.
Karpawich, P P, et al., "Altered cardiac histology following apical right ventricular pacing in patients with congenital atrioventricular block", Pacing Clin Electrophysiol., 22(9), (Sep. 1999), 1372-7.
Kendrick, J E, "A comparison of the cardiovascular responses to stimulation of the aortic and carotid sinus nerves of the dog", Proceedings of the Society for Experimental Biology & Medicine, 144(2), (Nov. 1973), 404-11.
Kieval, R., et al., "Devices and Methods for Cardiovascular Reflex Control", U.S. Appl. No. 60/368,222, filed Mar. 27, 2002, 146 pgs.
Kieval, Robert, et al., "Devices and Methods for Cardiovascular Reflex Control", U.S. Appl. No. 10/284,063, filed Oct. 29, 2002, 52 pgs.
Kramer, Andrew P, et al., U.S. Appl. No. 12/840,981, filed Jul. 21, 2010, 77 pgs.
Leclercq, C, et al., "Hemodynamic importance of preserving the normal sequence of ventricular activation in permanent cardiac pacing", Am Heart J., 129(6), (Jun. 1995), 1133-41.
Leutmezer, F, et al., "Electrocardiographic Changes at the onset of Epileptic Seizures", Epilepsia, 44(3), (2003), 348-354.
Li, M., et al., "Vagal nerve stimulation markedly improves long-term survival after chronic heart failure in rats", Circulation, 109(1), (2004), 120-124.
Libbus, I., et al., "Hypertension Therapy Based on Activity and Circadian Rhythm", U.S. Appl. No. 12/968,797, filed Dec. 15, 2010, 75 pgs.
Libbus, I., "Integrated Lead for Applying Cardiac Resynchronization Therapy and Neural Stimulation Therapy", U.S. Appl. No. 11/077,970, filed Mar. 11, 2005, 67 pgs.
Libbus, I., et al., "Method and Apparatus for Synchronizing Neural Simulation to Cardiac Cycles", U.S. Appl. No. 11/099,141, filed Apr. 5, 2005, 36 pgs.
Libbus, I., et al., "System and Method for Closed-Loop Neural Stimulation", U.S. Appl. No. 10/992,319, filed Nov. 18, 2004, 50 pgs.
Libbus, Imad, "Baroreflex Activation Therapy With Conditional Shut Off", U.S. Appl. No. 12/783,119, filed May 19, 2010, 94 pgs.
Libbus, Imad, "Automatic Baroreflex Modulation Based on Cardiac Activity", U.S. Appl. No. 10/746,846, filed Dec. 24, 2003, 75 pgs.
Libbus, Imad, "Automatic Baroreflex Modulation Responsive to Adverse Event", U.S. Appl. No. 10/745,925, filed Dec. 24, 2003, 73 pgs.
Libbus, Imad, "Automatic Neural Stimulation Modulation Based on Activity", U.S. Appl. No. 11/558,083, filed Nov. 9, 2006, 76 pgs.
Libbus, Imad, et al., "Baropacing and Cardiac Pacing to Control Output", U.S. Appl. No. 10/746,135, filed Dec. 24, 2003, 68 pgs.
Libbus, Imad, "Baroreflex Modulation Based on Monitored Cardiovascular Parameter", U.S. Appl. No. 10/939,544, filed Sep. 13, 2004, 75 pgs.
Libbus, Imad, et al., "Baroreflex Modulation to Gradually Decrease Blood Pressure", U.S. Appl. No. 10/746,845, filed Dec. 24, 2003, 72 pgs.
Libbus, Imad, "Baroreflex Stimulation Synchronized to Circadian Rhythm", U.S. Appl. No. 10/746,844, filed Dec. 24, 2003, 70 pgs.
Libbus, Imad, "Baroreflex Stimulation to Treat Acute Myocardial Infarction", U.S. Appl. No. 10/745,920, filed Dec. 24, 2003, 70 pgs.
Libbus, Imad, "Baroreflex Stimulator With Integrated Pressure Sensor", U.S. Appl. No. 10/745,921, filed Dec. 24, 2003, 72 pgs.
Libbus, Imad, "Baroreflex Therapy for Disordered Breathing", U.S. Appl. No. 10/864,070, filed Jun. 8, 2004, 71 pgs.
Libbus, Imad, "Cardiac Rhythm Management Device With Neural Sensor", U.S. Appl. No. 10/992,320, filed Nov. 18, 2004, 65 pgs.
Libbus, Imad, "Implantable Device for Treating Epilepsy and Cardiac Rhythm Disorders", U.S. Appl. No. 11/312,178, filed Dec. 21, 2005, 39 pgs.
Libbus, Imad, "Neural Stimulation With Avoidance of Inappropriate Stimulation", U.S. Appl. No. 11/000,249, filed Nov. 30, 2004, 45 pgs.
Libbus, Imad, et al., "Sensing With Compensation for Neural Stimulator", U.S. Appl. No. 11/621,194, filed Jan. 9, 2007, 69 pgs.
Libbus, Imad, et al., "Sensing With Compensation for Neural Stimulator", U.S. Appl. No. 10/746,847, filed Dec. 24, 2003, 71 pgs.
Libbus, Imad, "Stimulator for Auricular Branch of Vagus Nerve", U.S. Appl. No. 11/005,703, filed Dec. 7, 2004, 35 pgs.
Libbus, Imad, "System and Method for Sustained Baroreflex Stimulation", U.S. Appl. No. 10/962,845, filed Oct. 12, 2004, 50 pgs.
Libbus, Imad, "System to Provide Myocardial and Neural Stimulation", U.S. Appl. No. 11/087,935, filed Mar. 23, 2005, 52 pgs.
Mannheimer, C, et al., "Epidural spinal electrical stimulation in severe angina pectoris", British Heart Journal, 59(1), (Jan. 1988), 56-61.
Mannheimer, C, et al., "Transcutaneous electrical nerve stimulation (TENS) in angina pectoris", Pain, 26(3), (Sep. 1986), 291-300.
Mannheimer, C, et al., "Transcutaneous electrical nerve stimulation in severe angina pectoris", European Heart Journal, 3(4), (Aug. 1982), 297-302.
Mazgalev, T N, et al., "Autonomic modification of the atrioventricular node during atrial fibrillation: role in the slowing of ventricular rate", Circulation, 99(21), (Jun. 1, 1999), 2806-14.
McGregor, A., et al., "Right-Sided Vagus Nerve Stimulation as a Treatment for Refractory Epilepsy in Humans", Epilepsia; 46(1), (Jan. 2005), 91-96.
McMahon, N. C., et al., "Reflex responses from the main pulmonary artery and bifurcation in anaesthetised dogs.", Experimental Physiology, 85(4), (2000), 411-420.
Millar-Craig, M W, et al., "Circadian variation of blood-pressure", Lancet, 1(8068), (Apr. 15, 1978), 795-7.
Minisi, A J, et al., "Regional left ventricular deafferentation increases baroreflex sensitivity following myocardial infarction", Cardiovasc Res., 58(1), (Apr. 1, 2003), 136-41.
Moffitt, Julia, "Combined Neural Stimulation and Cardiac Resynchronization Therapy", U.S. Appl. No. 11/078,460, filed Mar. 11, 2005, 35 pgs.
Murphy, D F, et al., "Intractable angina pectoris: management with dorsal column stimulation", Medical Journal of Australia, 146(5), (Mar. 2, 1987), 260.
Neistadt, A, et al., "Effects of electrical stimulation of the carotid sinus nerve in reversal of experimentally induced hypertension", Surgery, 61(6), (Jun. 1967), 923-31.
Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.
Pastore, Joseph M., et al., "Multi-Site Ventricular Pacing Therapy With Parasympathetic Stimulation", U.S. Appl. No. 10/700,368, filed Nov. 3, 2003, 18 pgs.
Pauza, D. H., et al., "Morphology, distribution, and variability of the epicardiac neural ganglionated subplexuses in the human heart", The Anat. Rec. 259(4), (2000), 353-382.
Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.

Peters, T K, et al., "The principle of electrical carotid sinus nerve stimulation: a nerve pacemaker system for angina pectoris and hypertension therapy", Annals of Biomedical Engineering, 8(4-6), (1980), 445-58.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

Prakash, P, et al., "Asymmetrical distribution of aortic nerve fibers in the pig", Anat Rec., 158(1), (May 1967), 51-7.

Rosenqvist, M, et al., "The effect of ventricular activation sequence on cardiac performance during pacing", Pacing and Electrophysiology, 19(9), (1996), 1279-1286.

Rugg-Gunn, F. J, et al., "Cardiac arrhythmias in focal epilepsy: a prospective long-term study.", Lancet, 364(9452), (Dec. 18-31, 2004), 2212-9.

Rushmer, Robert F, "Chapter 5—Systemic Arterial Pressure", In: Cardiovascular dynamics, Philadelphia : Saunders, (1976), 176-216.

Schauerte, P, et al., "Catheter stimulation of cardiac parasympathetic nerves in humans: a novel approach to the cardiac autonomic nervous system", Circulation, 104(20), (Nov. 13, 2001), 2430-5.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Transvenous Parasympathetic Nerve Stimulation in the Inferior Vena Cava and Atrioventricular Conduction", Journal of Cardiovascular Electrophysiology, 11(1), (Jan. 2000), 64-69.

Scheiner, Avram, "Stimulation Lead for Stimulating the Baroreceptors in the Pulmonary Artery", U.S. Appl. No. 10/746,852, filed Dec. 24, 2003, 25 pgs.

Scherlag, B. J, et al., "Endovascular stimulation within the left pulmonary artery to induce slowing of heart rate and paroxysmal atrial fibrillation.", Cardiovasc Research, 54(2), (May 2002), 470-475.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Schmidt, E M, "Blood pressure response to aortic nerve stimulation in swine", American Journal of Physiology, 215(6), (Dec. 1968), 1488-92.

Sigurdsson, A., et al., "The Role of Neurohormonal Activation in Chronic Heart Failure and Postmyocardial Infarction", American Heart Journal, 132(1, Part 2), (Jul. 1996), 229-234.

Takahashi, N, et al., "Vagal modulation of ventricular tachyarrhythmias induced by left ansae subclaviae stimulation in rabbits", Japanese Heart Journal, 39(4), (Jul. 1998), 503-11.

Thompson, Gregory W, "Bradycardia induced by intravascular versus direct stimulation of the vagus nerve", Annals of Thoracic Surgery, 65(3), (Mar. 1998), 637-642.

Tse, H F, et al., "Long-term effect of right ventricular pacing on myocardial perfusion and function", J Am Coll Cardiol., 29(4), (Mar. 15, 1997), 744-9.

Vanoli, E., et al., "Vagal Stimulation and Prevention of Sudden Death in Conscious Dogs With a Healed Myocardial Infarction", Circulation Research, 68(5), (May 1991), 1471-1481.

Veerman, D P, et al., "Circadian profile of systemic hemodynamics", Hypertension, 26(1), (Jul. 1995), 55-9.

Verity, M A, et al., "Plurivesicular nerve endings in the pulmonary artery", Nature, 211(48), (Jul. 30, 1966), 537-8.

Verity, M, et al., "Pulmonary artery innervation: a morphopharmacologic correlation", Proceedings of the Western Pharmacology Society, 8, (1965), 57-9.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Waninger, M S, et al., "Electrophysiological control of ventricular rate during atrial fibrillation", Pacing & Clinical Electrophysiology, 23(8), (Aug. 2000), 1239-44.

Wiggers, C J, et al., "The muscular reactions of the mammalian ventricles to artificial surface stimuli", American Journal of Physiology, (1925), 346-378.

Zamotrinsky, A V, et al., "Vagal neurostimulation in patients with coronary artery disease", Autonomic Neuroscience-Basic & Clinical, 88(1-2), (Apr. 12, 2001), 109-116.

Zarse, Markus, et al., "Selective Increase of Cardiac Neuronal Sympathetic Tone—A Catheter-Based Access to Modulate Left Ventricular Contractility", Journal of the American College Cardiology, 46(7), (Oct. 4, 2005), 1354-1359.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

U.S. Appl. No. 10/746,852, Notice of Allowance mailed Oct. 18, 2011, 8 pgs.

U.S. Appl. No. 10/746,852, Response filed Sep. 7, 2011 to Final Office Action mailed Jul. 27, 2011, 8 pgs.

U.S. Appl. No. 11/276,107 , Response filed Nov. 29, 2012 to Non Final Office Action mailed Jun. 7, 2012, 11 pgs.

U.S. Appl. No. 11/276,107, Examiner Interview Summary mailed Jun. 7, 2012, 2 pgs.

U.S. Appl. No. 11/276,107, Examiner Interview Summary mailed Nov. 30, 2012, 3 pgs.

U.S. Appl. No. 11/276,107, Non Final office Action mailed Jun. 7, 2012, 10 pgs.

U.S. Appl. No. 11/276,107, Response filed Sep. 8, 2011 to Final Office Action mailed Jun. 15, 2011, 9 pgs.

* cited by examiner

LEAD FOR STIMULATING THE BARORECEPTORS IN THE PULMONARY ARTERY

CROSS REFERENCE TO RELATED APPLICATIONS

This application is a continuation of and claims the benefit of priority under 35 U.S.C. §120 to U.S. patent application Ser. No. 10/746,861, entitled "Lead for Stimulating the Baroreceptors in the Pulmonary Artery," filed on Dec. 24, 2003, now issued as U.S. Pat. No. 8,024,050, which is hereby incorporated by reference herein in its entirety.

The following commonly assigned U.S. patent applications are related, are all filed on the same date as the present application and are all herein incorporated by reference in their entirety: "Baroreflex Stimulation System to Reduce Hypertension," Ser. No. 10/746,134, now issued as U.S. Pat. No. 7,643,875; and "Stimulation Lead for Stimulating the Baroreceptors in the Pulmonary Artery," Ser. No. 10/746,852.

FIELD

This application relates generally to implantable medical devices and, more particularly, to systems, devices and methods for reducing hypertension using baroreceptor stimulation.

BACKGROUND

Medical leads have a distal end having one or more electrodes and a proximal end having a terminal that is coupled to a pulse generator. Electrical therapy is delivered from the pulse generator to the body via the electrode.

Hypertension is a cause of heart disease and other related cardiac co-morbidities. Hypertension occurs when blood vessels constrict. As a result, the heart works harder to maintain flow at a higher blood pressure, which can contribute to heart failure. Many patients who suffer from hypertension do not respond to treatment, such as treatments related to lifestyle changes and hypertension drugs.

A pressoreceptive region is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activate baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

The general concept of stimulating afferent nerve trunks leading from baroreceptors is known. For example, direct electrical stimulation has been applied to the vagal nerve and carotid sinus using nerve cuffs. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

What is needed is a less invasive technique for providing long-term electrical stimulation of the baroreflex.

SUMMARY

One aspect includes a method. The method includes implanting an expandable electrode within a pulmonary artery such that an outer surface of the expandable electrode abuts a wall of the pulmonary artery, the expandable electrode comprising a plurality of electrode zones, each zone individually coupled to a separate conductor of the lead body; testing each of the electrode zones to determine which zone delivers the best baroreflex response; selecting at least one of the electrode zones based on the testing; and delivering a baroreflex stimulation signal to a baroreceptor in the pulmonary artery via the one or more selected electrodes, wherein the implantable pulse generator is programmed such that the signal is delivered for about 5 seconds to about 10 seconds each minute at a voltage of about 0.1 volts to about 10 volts and a frequency of about 10 Hz to 150 Hz.

DETAILED DESCRIPTION

Figure 1:
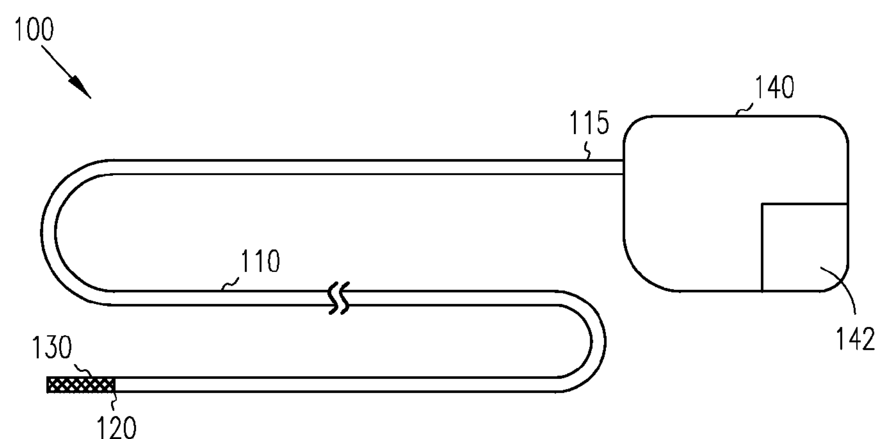
FIG. 1 shows a lead and pulse generator, in accordance with one embodiment.

The following detailed description and accompanying drawings show specific embodiments in which the present invention may be practiced. These embodiments are described in sufficient detail to enable those skilled in the art to practice the invention. Other embodiments may be utilized and structural changes may be made without departing from the scope of the present invention.

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The subject matter of this disclosure generally refers to the effects that the ANS has on the heart rate and blood pressure, including vasodilation and vasoconstriction. The heart rate and force is increased when the sympathetic nervous system is stimulated, and is decreased when the sympathetic nervous system is inhibited (e.g. when the parasympathetic nervous system is stimulated).

Baroreflex is a reflex triggered by stimulation of a baroreceptor. A baroreceptor includes any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Additionally, a baroreceptor includes afferent nerve trunks, such as the vagus, aortic and carotid nerves, leading from the sensory nerve endings. Stimulating baroreceptors inhibits sympathetic nerve activity (stimulates the parasympathetic nervous system) and reduces systemic arterial pressure by decreasing peripheral vascular resistance. Baroreceptors are naturally stimulated by internal pressure and the stretching of the arterial wall.

Some aspects of the present subject matter locally and directly stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites in the aorta.

FIG. 1 shows a lead 100 according to one embodiment. Lead 100 includes a flexible lead body 110 extending from a proximal end 115 to a distal end 120. An expandable electrode 130 is coupled proximate the distal end 120 of lead body 110. As will be discussed below, electrode 130 is adapted to deliver stimulation to baroreceptors in the pulmonary artery. For example, the expandable electrode 130 can have an expanded diameter dimensioned to abut a wall of a pulmonary artery to hold the electrode in place without any active fixation.

Lead 100 is coupled to an implantable pulse generator 140. Lead 100 includes conductors, such as coiled conductors that electrically couple pulse generator 140 to expandable electrode 130. Accordingly, implantable pulse generator 140 can deliver a baroreflex stimulation signal to a baroreceptor in the pulmonary artery via the electrode 130. The lead further includes outer insulation to insulate the conductor. The system can include a unipolar system with the case acting as an electrode or a bipolar system with a pulse between two distally located electrodes.

In one embodiment, pulse generator 140 includes hardware, circuitry and software to perform NS functions. Some embodiments can also perform an AHT function. Pulse generator includes controller circuitry 142. The controller circuitry 142 is capable of being implemented using hardware, software, and combinations of hardware and software. For example, according to various embodiments, the controller circuitry 142 includes a processor to perform instructions embedded in a memory to perform functions associated with NS therapy such as AHT therapy. In one example, the pulse generator delivers a pulse train having a frequency of between 10 to 150 hertz via the electrode.

Figure 2:
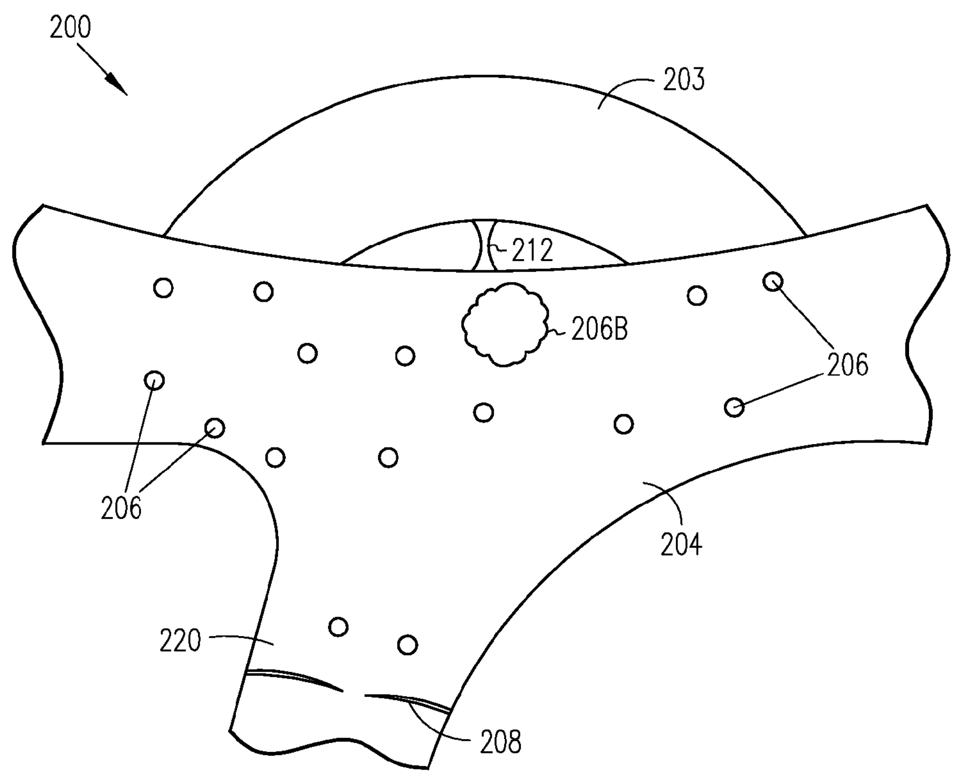
FIG. 2 shows details of a heart.

FIG. 2 shows a representation of a portion of a heart 200. Heart 200 includes an aortic arch 203 and a pulmonary artery 204. Pulmonary artery 204 includes a plurality of baroreceptors 206. A lead, such as lead 100 (FIG. 1), is capable of being intravascularly inserted through a peripheral vein and through the tricuspid valve into the right ventricle of the heart (not expressly shown in the figure) similar to a cardiac pacemaker lead, and continue from the right ventricle through the pulmonary valve 208 into the pulmonary artery 204.

A portion of the pulmonary artery 204 and aorta arch 203 are proximate to each other. According to various aspects of the present subject matter, the baroreflex is stimulated in or around the pulmonary artery by at least one electrode intravascularly inserted into the pulmonary artery. Aspects of the present subject matter provide a relatively noninvasive surgical technique to implant a baroreceptor stimulator intravascularly into the pulmonary artery. The baroreceptors 206, for example, are sensitive to stretching of the wall resulting from increased pressure from within. Activation of these nerve endings reduce pressure.

As illustrated, the pulmonary artery 204 includes a number of baroreceptors 206, as generally indicated by the dark areas. Furthermore, a cluster of closely spaced baroreceptors 206B are situated near the attachment of the ligamentum arterio sum 212. According to various embodiments of the present subject matter, a lead is inserted through a peripheral vein and threaded through the tricuspid valve into the right ventricle, and from the right ventricle through the pulmonary valve 208 and into the pulmonary artery 204 to simulate baroreceptors in and/or around the pulmonary artery. In various embodiments, for example, the lead is positioned in the artery to stimulate the cluster of baroreceptors 206B near the ligamentum arterio sum 212.

There are also baroreceptor fields in the aortic arch 203, near the ligamentum arterio sum 212, and in the trunk 220 of the pulmonary artery 204. Some embodiments position the lead in the pulmonary artery to stimulate baroreceptor sites in the aorta, possibly via the ligamentum arteriosum 212, or in the pulmonary trunk, or in either the right or left pulmonary arteries.

Figure 3:
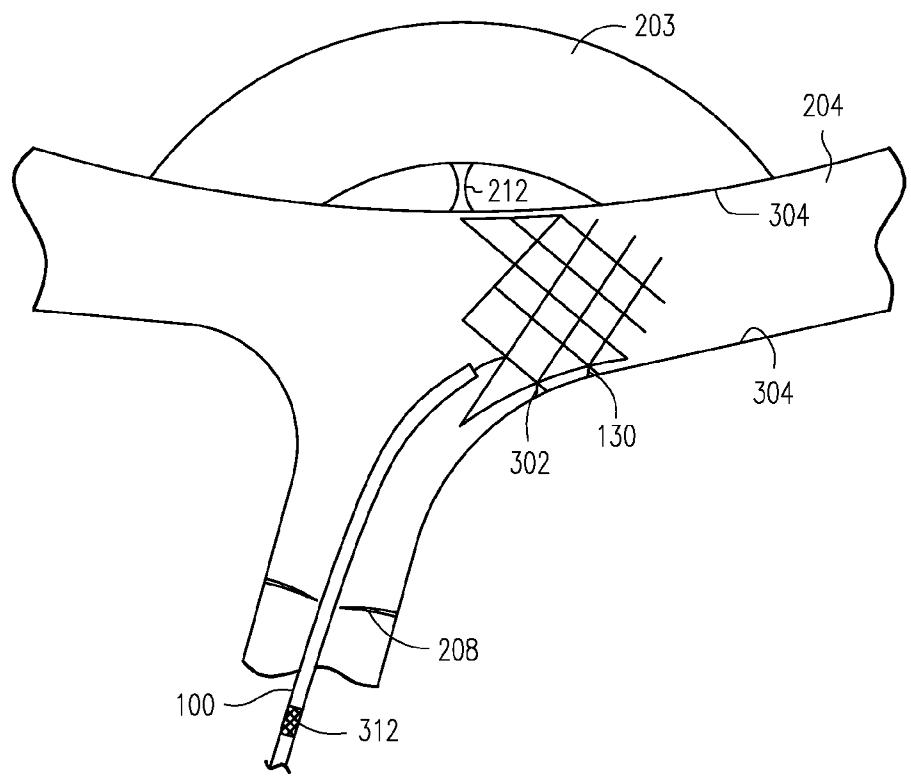
FIG. 3 shows the lead of FIG. 1 implanted in a heart, in accordance with one embodiment.

FIG. 3 shows expandable electrode 130 mounted in pulmonary artery 204, in accordance with one embodiment. In one embodiment, expandable electrode 130 is a stent-like structure including a mesh surface 302. The expandable electrode is designed to expand to abut the outer walls 304 of the pulmonary artery so as to passively fixate the lead and the electrode in place by frictional forces. In this example, the electrode is adapted to be located near the ligamentum arteriosum 212 of the left pulmonary artery 204.

Expandable electrode 130 can have various shapes and sizes. In one embodiment, the length to diameter ratio is smaller than in typical stents. For example, one embodiment includes a length of at least about 1 cm. Other examples can be up to 3 cm or greater. The diameter of the electrode 130 in its expanded orientation can range from about 10 mm to about 20 mm. Other embodiments can have a larger diameter. In general, the electrode is dimensioned to provide direct, low-voltage, high-frequency nerve stimulation.

In one embodiment, lead 100 can include a second electrode 312 located proximally from the expandable electrode 130. This electrode can be used for bradyarrhythmia therapy, tachyarrhythmia therapy, as a sensing electrode, or as a cathode for electrode 130.

In one example, electrode 130 is adapted to be chronically implanted in the pulmonary artery. For example, by passively mounting the electrode within the artery, no long-term damage is done to the artery.

Figure 4:
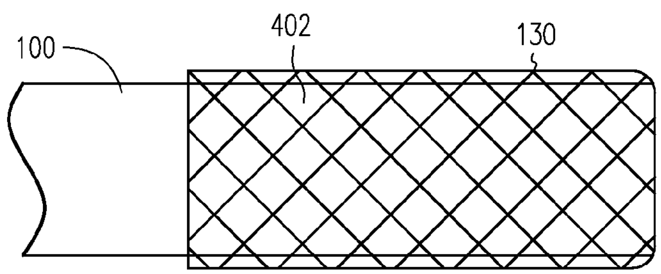
FIG. 4 shows a lead having an expandable electrode in accordance with one embodiment.
Figure 5:
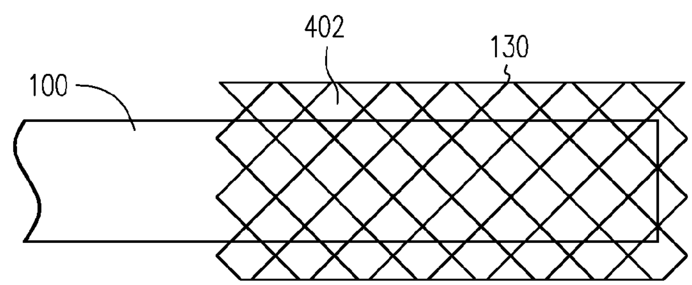
FIG. 5 shows the lead of FIG. 4 with the electrode in an expanded configuration.

FIGS. 4 and 5 show lead 100, in accordance with one embodiment. Lead 100 can include an inflatable balloon 402 that can be inflated once the electrode is positioned correctly. Inflating the balloon 402 expands the electrode 130 until the electrode abuts the walls of the artery, as discussed above.

Figure 6:
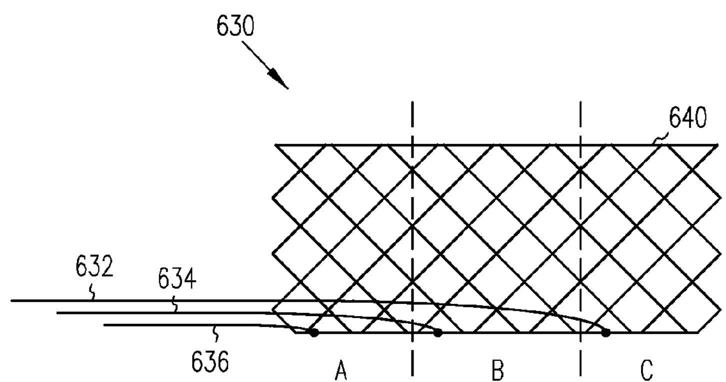
FIG. 6 shows an expandable electrode in accordance with one embodiment.

FIG. 6 shows an expandable electrode 630, in accordance with one embodiment. Electrode 630 can be used in place of electrode 130 discussed above. Electrode 630 includes an outer surface 640 that can be at least partially masked so as to be electrically non-conductive. For example, electrode 630 has been marked off into zones A, B, and C. Zones A, B, and C can have varying sizes and shapes and the zones shown are an example. In one example, sections A and C can be electrically conductive and zone B is masked off. Alternatively, any of the sections or portions can be electrically insulated.

In one embodiment, none of sections A, B, or C is masked off and each is coupled to a separate conductor 632, 634, and 636 of lead 100 (FIG. 1). In this example, the user implants the electrode and then tests each zone separately to discover which gives the best baroreflex response. Then, the non-productive zones can be turned off, or used for sensing, for example.

Figure 7:
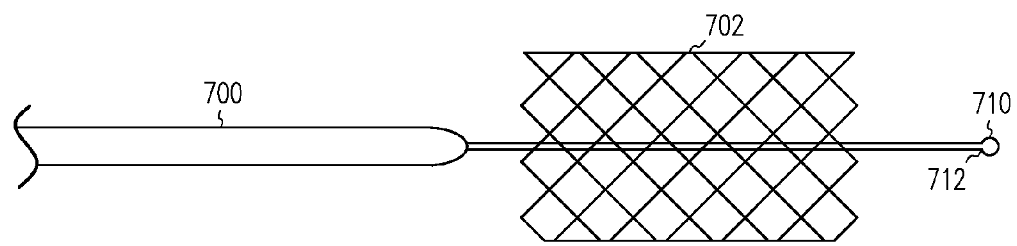
FIG. 7 shows a side view of a lead in accordance with one embodiment.

FIG. 7 illustrates a baroreceptor stimulation lead 700 with an integrated pressure sensor 710 (IPS) and an expandable electrode 702, according to various embodiments of the present subject matter. In one example, lead 700 can include an IPS 710 with a baroreceptor stimulator electrode 712 to monitor changes in blood pressure, and thus to monitor the effect of the baroreceptor stimulation. In various embodiments, micro-electrical mechanical systems (MEMS) technology can be used to sense the blood pressure. Some sensor embodiments determine blood pressure based on a displacement of a membrane.

In one example use of lead 700, a system can include baroreceptor stimulation circuitry and sensor circuitry. The circuitry can be within pulse generator 140 (FIG. 1) or be a separate system communicating wirelessly with the pulse generator. One or more leads can be connected to the sensor circuitry and baroreceptor stimulation circuitry. The baroreceptor stimulation circuitry is used to apply electrical stimulation pulses to desired baroreceptors sites, such as baroreceptor sites in the pulmonary artery, through one or more stimulation electrodes, such as electrodes 702 or 712. The sensor circuitry is used to detect and process ANS nerve activity and/or surrogate parameters such as blood pressure, respiration and the like, to determine the ANS activity.

Lead 700, for example, is capable of being intravascularly introduced to stimulate a baroreceptor site, such as the baroreceptor sites in the pulmonary artery, aortic arch, or ligamentum arteriosum. One or more additional electrodes can be provided to pace and/or sense cardiac activity, such as that which may occur within the right ventricle with the sensor 710 located near baroreceptors in or near the pulmonary artery and programmed to stimulate and sense, either directly or indirectly through surrogate parameters, baroreflex activity.

To provide hypertension therapy according to one embodiment, a lead, such as lead 100, is intravascularly inserted through a peripheral vein and through the tricuspid valve into the right ventricle of the heart and then from the right ventricle through the pulmonary valve into the pulmonary artery. An electrode on the lead is fixated to a region of the pulmonary artery having one or more baroreceptors. One example passively fixates the electrode proximate the ligamentum arteriosum of the left pulmonary artery. In one embodiment, the pulse generator is designed to intermittently pace the baroreceptor with a low-voltage, high frequency pulse train. For example, the baroreceptor can be paced for about 5 to 10 seconds each minute at a voltage of about 0.1 volts to 10 volts and a frequency between about 10 Hz and 150 Hz. Some examples utilize a voltage between about 1 volt to about 10 volts.

As noted, further embodiments can include a sensor to monitor blood pressure. The sensor can sense a physiological parameter regarding an efficacy of the baroreflex therapy and provides a signal indicative of the efficacy of the baroreflex therapy. For example, a controller can be connected to a pulse generator to control the baroreflex stimulation signal and to the sensor to receive the signal indicative of the efficacy of the baroreflex therapy. In some examples, the pulse generator can be further adapted to generate a cardiac pacing signal, and the lead can include a second electrode to be positioned to deliver the cardiac pacing signal to capture the heart. The present expandable electrode allows for chronically indwelling, is easy to implant, and is safe and reliable.

In various embodiments of baroreceptor pacing according to the present subject matter, the system can deliver the pulse train intermittently with no sensing, or the system can be activated by the user when the user is at rest, or it can be activated by a timer to be periodically turned off and on, or it can be activated when the user goes to sleep, for example.

According to various embodiments, the stimulator circuitry and sensing circuitry of the present system can include one or more functions as described in the commonly assigned U.S. patent application filed on the same date as the present application and incorporated by reference in its entirety: "Baroreflex Stimulation System to Reduce Hypertension," Ser. No. 10/746,134, filed on Dec. 24, 2003.

For example, various embodiments of the present subject matter relate to baroreflex stimulator systems. Such baroreflex stimulation systems are also referred to herein as neural stimulator (NS) devices or components. Examples of neural stimulators include anti-hypertension (AHT) devices or AHT components that are used to treat hypertension. Various embodiments of the present subject matter include standalone implantable baroreceptor stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Integrating NS and CRM functions that are either performed in the same or separate devices improves aspects of the NS therapy and cardiac therapy by allowing these therapies to work together intelligently.

Thus, various embodiments of the present subject matter provide an implantable NS device that automatically modulates baroreceptor stimulation using an IPS. Integrating the pressure sensor into the lead provides localized feedback for the stimulation. This localized sensing improves feedback control. For example, the integrated sensor can be used to compensate for inertia of the baroreflex such that the target is not continuously overshot. According to various embodiments, the device monitors pressure parameters such as mean arterial pressure, systolic pressure, diastolic pressure and the like. As mean arterial pressure increases or remains above a programmable target pressure, for example, the device stimulates baroreceptors at an increased rate to reduce blood pressure and control hypertension.

As mean arterial pressure decreases towards the target pressure, the device responds by reducing baroreceptor stimulation. In various embodiments, the algorithm takes into account the current metabolic state (cardiac demand) and adjusts neural stimulation accordingly. A NS device having an IPS is able to automatically modulate baroreceptor stimulation, which allows an implantable NS device to determine the level of hypertension in the patient and respond by delivering the appropriate level of therapy. However, it is noted that other sensors, including sensors that do not reside in an NS or neural stimulator device, can be used to provide close loop feedback control.

An aspect of the present subject matter relates to a chronically-implanted stimulation system specially designed to treat hypertension by monitoring blood pressure and stimulating baroreceptors to activate the baroreceptor reflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. In various embodiments, the system is integrated into a pacemaker/defibrillator or other electrical stimulator system. Components of the system include a high-frequency pulse generator, sensors to monitor blood pressure or other pertinent physiological parameters, leads to apply electrical stimulation to baroreceptors, algorithms to determine the appropriate time to administer stimulation, and algorithms to manipulate data for display and patient management.

Various embodiments relates to a system that seeks to deliver electrically mediated NS therapy, such as AHT therapy, to patients. Various embodiments combine a "stand-alone" pulse generator with a minimally invasive, unipolar lead that directly stimulates baroreceptors in the vicinity of the heart, such as in the pulmonary artery. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial baroreceptor tissues using transvenous implant technique (s).

Another embodiment includes a system that combines NS therapy with traditional bradyarrhythmia, tachyarrhythmia, and/or congestive heart failure (CHF) therapies. Some embodiments use an additional "baroreceptor lead" that emerges from the device header and is paced from a modified traditional pulse generating system. In another embodiment, a traditional CRM lead is modified to incorporate proximal electrodes that are naturally positioned near baroreceptor sites. With these leads, distal electrodes provide CRM therapy and proximal electrodes stimulate baroreceptors.

Various embodiments of the present subject matter relate to a method of sensing atrial activation and confining pulmonary artery stimulation to the atrial refractory period, preventing unintentional stimulation of nearby atrial tissue. An implantable baroreceptor stimulation device monitors atrial activation with an atrial sensing lead. A lead in the pulmonary artery stimulates baroreceptors in the vessel wall. However, instead of stimulating these baroreceptors continuously, the stimulation of baroreceptors in the pulmonary artery occurs during the atrial refractory period to avoid capturing nearby atrial myocardium, maintaining the intrinsic atrial rate and activation. Various embodiments of the present subject matter combine an implantable device for stimulating baroreceptors in the wall of the pulmonary artery with the capability for atrial sensing.

In some embodiments, the pulse generator can include a transceiver and associated circuitry for use to communicate with a programmer or another external or internal device. Various embodiments have wireless communication capabilities. For example, some transceiver embodiments use a telemetry coil to wirelessly communicate with a programmer or another external or internal device.

The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:

implanting an expandable electrode within a pulmonary artery such that an outer surface of the expandable electrode abuts a wall of the pulmonary artery, the expandable electrode comprising a plurality of electrode zones, each zone individually coupled to a separate conductor of the lead body;

testing each of the electrode zones to determine which zone delivers the best baroreflex response;

selecting at least one of the electrode zones based on the testing; and delivering a baroreflex stimulation signal to a baroreceptor in the pulmonary artery via the one or more selected electrodes, wherein the implantable pulse generator is programmed such that the signal is delivered for about 5 seconds to about 10 seconds each minute at a voltage of about 0.1 volts to about 10 volts and a frequency of about 10 Hz to 150 Hz.

2. The method of claim 1, wherein implanting includes implanting an expandable electrode having an expanded diameter dimensioned to fix the electrode in place by frictional forces.

3. The method of claim 1, wherein the electrode is adapted to be chronically implanted in the pulmonary artery.

4. The method of claim 1, further including monitoring a blood pressure.

5. The method of claim 1, wherein implanting includes implanting the electrode proximate the ligamentum arteriosum of the left pulmonary artery.

6. The method of claim 1, wherein implanting includes feeding the electrode through a right ventricle and a pulmonary valve into the pulmonary artery to position the electrode in the pulmonary artery.

7. The method of claim 1, wherein implanting includes implanting an expandable electrode having an expanded diameter of about 10 to 20 mm.

8. The method of claim 1, wherein delivering a baroreflex stimulation signal includes an at least 10 hertz pulse train via the electrode.

9. The method of claim 1, wherein the expandable electrode includes a stent-like structure.

10. The method of claim 1, wherein each electrode zone individually coupled to a separate conductor within the lead body.

11. The method of claim 1, wherein the expandable electrode includes at least a partially electrically insulated surface.

12. The method of claim 1, further including sensing a physiological parameter regarding an efficacy of the baroreflex stimulation and providing a signal indicative of the efficacy of the baroreflex stimulation.

13. The method of claim 12, further including receiving the signal at a controller and using the controller to control the baroreflex stimulation pulse.

14. A method comprising:

providing a flexible lead body extending from a proximal end to a distal end with an expandable electrode coupled to the lead body, the expandable electrode comprising a plurality of electrode zones, each electrode zone individually coupled to a separate conductor within the lead body;

coupling the expandable electrode to an implantable pulse generator;

implanting the expandable electrode in a pulmonary artery proximate a baroreceptor;

testing each electrode zone separately to determine which electrode zone delivers the best baroreflex response;

selecting at least one of the electrode zones to deliver a baroreflex stimulation signal to the baroreceptor in the pulmonary artery to produce a baroreflex response; and delivering a baroreflex stimulation signal to the baroreceptor in the pulmonary artery via the at least one selected electrode zone, wherein the baroreflex stimulation signal is delivered for about 5 seconds to about 10 seconds each minute at a voltage of about 0.1 volts to about 10 volts and a frequency of about 10 Hz to 150 Hz.

15. The method of claim 14, wherein delivering the baroreflex stimulation signal includes delivering about a 10 hertz pulse train via the electrode.

16. The method of claim 14, wherein delivering the baroreflex stimulation signal to the baroreceptor causes a lowering of blood pressure.

17. The method of claim 14, wherein the expandable electrode comprises an expandable stent structure coupled to the lead body for passively fixating the expandable electrode in the pulmonary artery.

18. The method of claim 17, wherein the stent structure includes an expanded diameter dimensioned to abut a wall of the pulmonary artery.

* * * * *